(12) United States Patent
Kim et al.

(10) Patent No.: US 10,058,558 B2
(45) Date of Patent: Aug. 28, 2018

(54) PHARMACEUTICAL COMPOSITION COMPRISING N1-CYCLIC AMINE-N5-SUBSTITUTED BIGUANIDE DERIVATIVES AS AN INGREDIENT FOR PREVENTING OR TREATING FIBROSIS

(71) Applicant: ImmunoMet Therapeutics Inc., Houston, TX (US)

(72) Inventors: Sung Wuk Kim, Seongnam-si (KR); Soon Im Lee, Seoul (KR); Yeon Jung Song, Suwon-si (KR); Min Jae Shin, Seongnam-si (KR); Kook Hwan Oh, Seoul (KR); Kyung Don Ju, Seoul (KR); Eun Kyoung Shin, Seoul (KR); Ji Sun Lee, Daejeon (KR); Hye Jin Heo, Daejeon (KR); Hong Bum Lee, Daejeon (KR); Ji Ae Kook, Daejeon (KR); Min Jeong Kim, Seoul (KR); Hye Soun Eum, Seoul (KR)

(73) Assignee: ImmunoMet Therapeutics Inc., Houston, TX (US)

( * ) Notice: Subject to any disclaimer, the term of this patent is extended or adjusted under 35 U.S.C. 154(b) by 0 days.

(21) Appl. No.: 14/893,433

(22) PCT Filed: May 20, 2014

(86) PCT No.: PCT/KR2014/004474
§ 371 (c)(1),
(2) Date: Nov. 23, 2015

(87) PCT Pub. No.: WO2014/189246
PCT Pub. Date: Nov. 27, 2014

(65) Prior Publication Data
US 2016/0101112 A1    Apr. 14, 2016

(30) Foreign Application Priority Data
May 23, 2013 (KR) .................. 10-2013-0058493

(51) Int. Cl.
| | | |
|---|---|---|
| A61K 31/165 | (2006.01) | |
| A61K 31/55 | (2006.01) | |
| A61K 31/155 | (2006.01) | |
| C07C 279/26 | (2006.01) | |
| A61K 31/397 | (2006.01) | |
| A61K 31/40 | (2006.01) | |
| A61K 31/44 | (2006.01) | |
| A61K 31/445 | (2006.01) | |

(52) U.S. Cl.
CPC ............ *A61K 31/55* (2013.01); *A61K 31/155* (2013.01); *A61K 31/397* (2013.01); *A61K 31/40* (2013.01); *A61K 31/44* (2013.01); *A61K 31/445* (2013.01); *C07C 279/26* (2013.01)

(58) Field of Classification Search
None
See application file for complete search history.

(56) References Cited

U.S. PATENT DOCUMENTS 7,622,117 B2 * 11/2009 Tobia ...................... A61K 8/44
424/146.1

FOREIGN PATENT DOCUMENTS

| KR | 10-2013-0018622 A | 2/2013 | |
|---|---|---|---|
| KR | 10-2013-0019351 A | 2/2013 | |
| WO | WO 2005079463 A2 * | 9/2005 | ............ A61K 31/00 |
| WO | WO-2013/022278 A2 | 2/2013 | |
| WO | WO-2013/022279 A2 | 2/2013 | |
| WO | WO 2013022278 A2 * | 2/2013 | ........... C07D 205/04 |
| WO | WO 2013022279 A2 * | 2/2013 | ........... C07D 333/20 |

OTHER PUBLICATIONS

Hernandez-Gea et al., Pathogenesis of Liver Fibrosis, Annu. Rev. Pathol. Mech. Dis. 2011. 6: 425-56.*
Guggino et al, New insights into cystic fibrosis: molecular switches that regulate CFTR, Nature, Jun. 2006 (7): 426-436.*
Tak, Won Yeong, The Journal of Clinical and Molecular Hepatology, 2007, vol. 13, No. 4S, pp. S74-S78.
Boutet, A. et al. The EMBO Journal, 2006, vol. 25, pp. 5603-5613.
Willis, B.C. et al. American Journal of Physiology-Lung Cellular and Molecular Physiology, 2007, vol. 293, pp. L525-534.
Hutchison, Nicol, et al. Biochimica et Biophysica Acta, Jul. 2013; 1832(7): 962-971.
Derynck, Rik and Akhurst, Rosemary J. Nature Cell Biology, 9(9), 1000-1004, 2007.
International Search Report, dated Aug. 7, 2014 in connection with PCT International Application No. PCT/KR2014/004474, filed May 20, 2014.

* cited by examiner

*Primary Examiner* — Svetlana M Ivanova
(74) *Attorney, Agent, or Firm* — Clark & Elbing LLP

(57) ABSTRACT

The present invention provides a novel use of N1-cyclic amine-N5-substituted biguanide derivatives for preparing a medicine for preventing or treating fibrosis. The N1-cyclic amine-N5-substituted biguanide derivatives according to the present invention are capable of effectively inhibiting fibrosis by effectively suppressing the EMT.

10 Claims, 3 Drawing Sheets

[FIG. 1]
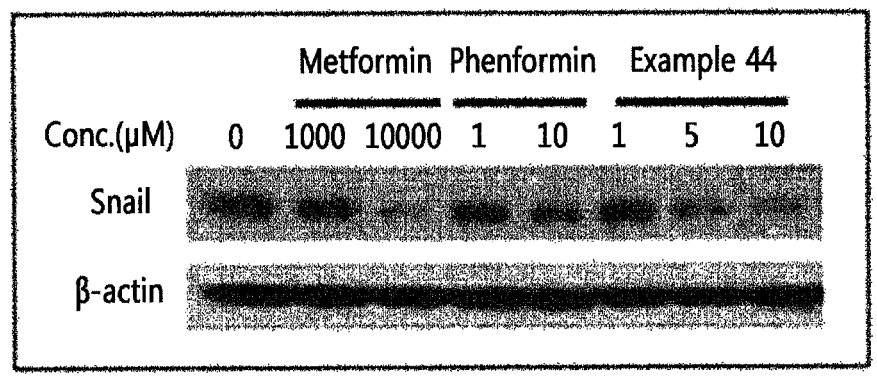
[FIG. 2]
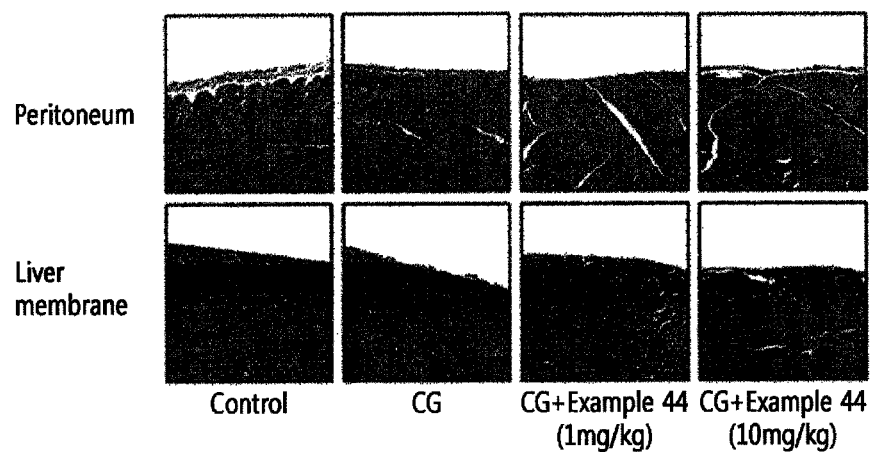

[FIG. 3]
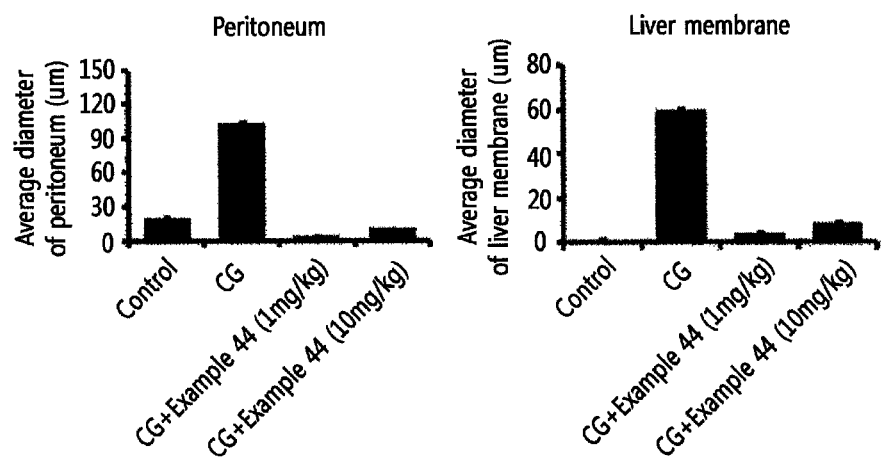

[FIG. 4]
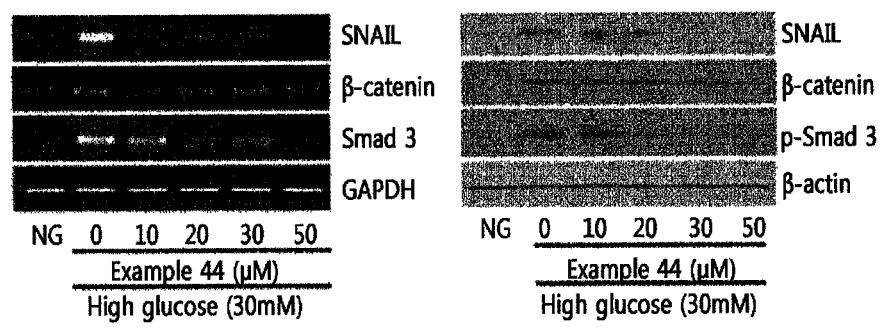
[FIG. 5]
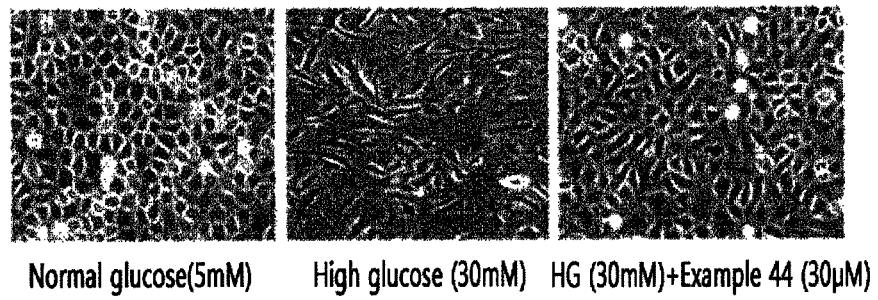
Normal glucose(5mM)   High glucose (30mM)   HG (30mM)+Example 44 (30μM)

PHARMACEUTICAL COMPOSITION COMPRISING N1-CYCLIC AMINE-N5-SUBSTITUTED BIGUANIDE DERIVATIVES AS AN INGREDIENT FOR PREVENTING OR TREATING FIBROSIS

CROSS-REFERENCE TO RELATED APPLICATIONS

This application is a § 371 national stage of PCT International Application No. PCT/KR2014/004474, filed May 20, 2014, claiming priority of Korean Patent Application No. 10-2013-0058493, filed May 23, 2013, the contents of each of which are hereby incorporated by reference in their entirety.

BACKGROUND OF THE INVENTION

1. Field of the Invention

The present invention relates to a novel use of a N1-cyclic amine-N5-substituted biguanide derivative in preparing a medicine for preventing or treating fibrosis.

2. Description of the Related Art

Fibrosis is a phenomenon characterized by hardening in part of an organ, and representative examples include pulmonary fibrosis or liver fibrosis. Fibrosis mostly occurs as a consequence of a disturbed damage healing process, after mental trauma or chronic inflammation. Although fibrosis occurs in most organs, in particular, it frequently occurs in the liver, lungs, kidneys, heart, eyes, skin, pancreas, intestine, bone marrow, etc., and more particularly, in the liver, lungs, skin, and kidneys, in general.

These organs share common characteristics of activation of abnormal fibroblasts and accumulation of extracellular matrix (ECM), and these characteristics cause damage to the functions of the organs because normal tissues are replaced by cicatricial tissues.

At present, a representative example of a major mechanism known to induce fibrosis is the epithelial-mesenchymal transition (EMT).

That is, in the case of epithelial or endothelial damage, various inflammatory factors in normal tissues become freed, the blood coagulation process initiates as a process of anti-fibrinolytic-coagulation, and white blood cells are aggregated near the wound area, thereby activating the pericyte-myofibroblast transition. As a result, extracellular matrices (ECM), i.e., myofibroblasts, fibroblasts, and mesenchymal cells, are formed, and collagen fibers regenerate blood vessels and tissues and remove scars, thereby accomplishing normalization. However, continuous stimulation induces excess accumulation of ECM, thus leading to fibrosis (Resident mesenchymal cells and fibrosis, Nicol Hutchison, Cecile Fligny, Jeremy S. Duffield, Biochimica et Biophysica Acta, 2012).

That is, it is known that a cell loses its polarity and changes its shape through the EMT process and thereby inhibits cytokeratins, E-cadherin, and tight junctions, which are epithelial markers, whereas activating vimentin, Snail/Slug, extracellular matrix, matrix metalloproteinase, and α-smooth muscle actin (α-SMA), which are mesenchymal markers, thereby causing fibrosis (Differentiation plasticity regulated by TGF-β family proteins in development and disease, Rik Derynck and Rosemary J. Akhurst, Nature Cell Biology, 9(9), 1000-1004, 2007).

SUMMARY OF THE INVENTION

The present inventors aimed to develop a medicinal component capable of suppressing the EMT process to thereby provide a novel use of the component as an active ingredient of a pharmaceutical medicine for preventing or treating fibrosis.

The present invention provides a novel use of a N1-cyclic amine-N5-substituted biguanide derivative compound of Formula 1 below in preparing a medicine for preventing or treating fibrosis, a pharmaceutical composition for preventing or treating fibrosis containing the N1-cyclic amine-N5-substituted biguanide derivative compound of Formula 1 below as an active ingredient, and a method for preventing or treating fibrosis including administering the N1-cyclic amine-N5-substituted biguanide derivative compound of Formula 1 below to a subject in need thereof:

[Formula 1]

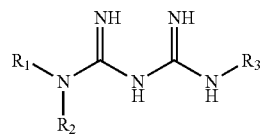

wherein in Formula 1, $R_1$ and $R_2$ are taken together with nitrogen to which they are attached to form 4- to 7-membered $C_{3-6}$ heterocycloalkyl or $C_{3-6}$ heterocycloalkene;

$R_3$ is H; $C_{3-7}$ cycloalkyl; $C_{3-12}$ aryl; or $C_{1-6}$ alkyl unsubstituted or substituted with $C_{3-12}$ aryl or $C_{3-12}$ heteroaryl;

wherein $C_{3-8}$ heterocycloalkyl, $C_{3-7}$ cycloalkyl, $C_{3-12}$ aryl, or $C_{3-12}$ heteroaryl is unsubstituted or substituted with at least one non-hydrogen substituent selected from the group consisting of halogen, $C_{1-4}$ alkyl, and $C_{1-4}$ alkoxy, and the non-hydrogen substituent is unsubstituted or further substituted with halogen.

As used herein, the term "a substituted group" refers to a group in which at least one hydrogen atom is replaced with at least one non-hydrogen atom group, provided that the group satisfies the valence requirements and forms a chemically stable compound from the substitution. Unless explicitly described as "unsubstituted", as used herein, it should be understood that all substituents will be unsubstituted or substituted with another substituent. The substituents $R_1$ to $R_3$ on the biguanide derivative according to the present invention may each be re-substituted with at least one of the substituents defined above.

The term "halogen" or "halo" refers to fluoro, chloro, bromo, and iodo.

The term "hydroxy" refers to —OH.

The term "alkyl" refers to a linear and branched saturated hydrocarbon group generally having a specified number of carbon atoms (e.g., 1 to 12 carbon atoms). Examples of the alkyl group may include, without limitation, methyl, ethyl, n-propyl, propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, n-octyl, etc. The alkyl may be attached to a parent group or a substrate at any ring atom unless the attachment would violate valence requirements. Likewise, the alkyl group may include at least one non-hydrogen substituent unless the substitution would violate valence requirements. For example, the term "haloalkyl" refers to —CH$_2$(halo), —CH(halo)$_2$, or C(halo)$_3$, i.e., a methyl group in which at least one hydrogen atom is replaced with halogen. Examples of the "haloalkyl" group may include, without limitation, trifluoromethyl, trichloromethyl, tribromomethyl, triiodomethyl, etc.

The term "alkoxy" refers to alkyl-O—, and alkyl is defined above. Examples of the alkoxy group may include, without limitation, methoxy, ethoxy, n-propoxy, i-propoxy, n-butoxy, s-butoxy, t-butoxy, n-pentoxy, s-pentoxy, etc. The alkoxy may be attached to a parent group or a substrate at any ring atom unless the attachment would violate valence requirements. Likewise, the alkoxy group may include at least one non-hydrogen substituent unless the substitution would violate valence requirements. For example, the term "haloalkoxy" refers to —O—$CH_2$(halo), —O—CH(halo)$_2$, or —O—C(halo)$_3$, i.e., a methoxy group in which at least one hydrogen atom is replaced with halogen. Examples of the "haloalkoxy" group may include, without limitation, trifluoromethoxy, trichloromethoxy, tribromomethoxy, tri-iodomethoxy, etc.

The term "cycloalkyl" refers to a saturated monocyclic and bicyclic hydrocarbon ring generally having a specified number of carbon atoms that includes a ring (i.e., $C_{3-8}$ cycloalkyl refers to a cycloalkyl group having 3, 4, 5, 6, 7, or 8 carbon atoms as a ring number). The cycloalkyl may be attached to a parent group or a substrate at any ring atom unless the attachment would violate valence requirements. Likewise, the cycloalkyl group may include at least one non-hydrogen substituent unless the substitution would violate valence requirements.

The term "heterocycloalkyl" refers to a monocyclic and bicyclic hydrocarbon ring having at least one heteroatom among the ring atoms of cycloalkyl, i.e., consisting of atoms including nitrogen, oxygen, and sulfur atoms other than carbon atoms. The heterocycloalkyl may be attached to a parent group or a substrate at any ring atom unless the attachment would violate valence requirements. Likewise, the heterocycloalkyl group may include at least one non-hydrogen substituent unless the substitution would violate valence requirements. Examples of the heterocycloalkyl group may include, without limitation, aziridine, azetidine, imidazolyl, pyrrolyl, pyrrolidinyl, piperidinyl, morpholinyl, piperazinyl, azepanyl, indolyl, indolinyl, etc.

The term "cycloalkene" refers to an unsaturated non-aromatic monocyclic and polycyclic hydrocarbon ring having a specified number of carbon atoms (i.e., $C_{3-8}$ cycloalkyl refers to a cycloalkene group having 3, 4, 5, 6, 7, or 8 carbon atoms as a ring number). The cycloalkene may be attached to a parent group or a substrate at any ring atom unless the attachment would violate valence requirements. Likewise, the cycloalkene group may include at least one non-hydrogen substituent unless the substitution would violate valence requirements.

The term "heterocycloalkene" refers to an unsaturated non-aromatic monocyclic and polycyclic hydrocarbon ring having at least one heteroatom among the ring atoms of cycloalkene, i.e., consisting of atoms including nitrogen, oxygen, and sulfur atoms other than carbon atoms. The heterocycloalkene may be attached to a parent group or a substrate at any ring atom unless the attachment would violate valence requirements. Likewise, the heterocycloalkene group may include at least one non-hydrogen substituent unless the substitution would violate valence requirements. Examples of the heterocycloalkene group may include, without limitation, dihydroazetine, dihydropyrrole, dihydropyridine, tetrahydropyridine, dihydroazepine, tetrahydroazepine, etc.

The term "aryl" refers to a monocyclic or bicyclic aromatic ring, and examples of the "aryl" group may include phenyl, naphthyl, anthryl, etc. The "aryl" group may be attached to a parent group or a substrate at any ring atom unless the attachment would violate valence requirements. Likewise, the aryl group may include at least one non-hydrogen substituent unless the substitution would violate valence requirements.

The term "heteroaryl" refers to a 5- to 10-membered aromatic hetero ring including both monocyclic and bicyclic rings. One to four heteroatoms independently selected from nitrogen, oxygen, and sulfur in heteroaryl are substituted with carbon atom(s). Examples of the heteroaryl group may include, without limitation, furanyl, pyrrolyl, thiophenyl, thiazolyl, isothiazolyl, imidazolyl, triazolyl, tetrazolyl, pyrazolyl, oxazolyl, isooxazolyl, pyridinyl, pyrazinyl, pyridazinyl, pyrimidinyl, isoquinolinyl, carbazolyl, benzoxazolyl, benzodioxazolyl, benzothiazolyl, benzoimidazolyl, benzothiophenyl, triazinyl, phthalazinyl, quinolinyl, indolyl, benzofuranyl, furinyl, and indolizinyl.

In an exemplary embodiment, $R_1$ and $R_2$ may be taken together with nitrogen to which they are attached to form 4- to 7-membered $C_{3-6}$ heterocycloalkyl or $C_{3-6}$ heterocycloalkene; and $R_3$ may be H; $C_{3-7}$ cycloalkyl; $C_{3-12}$ aryl; or $C_{1-6}$ alkyl unsubstituted or substituted with $C_{3-12}$ aryl or $C_{3-12}$ heteroaryl;

wherein $C_{3-8}$ heterocycloalkyl, $C_{3-7}$ cycloalkyl, $C_{3-12}$ aryl, or $C_{3-12}$ heteroaryl may be unsubstituted or substituted with at least one non-hydrogen substituent selected from the group consisting of halogen, $C_{1-4}$ alkyl, and $C_{1-4}$ alkoxy, and the non-hydrogen substituent may be unsubstituted or further substituted with halogen;

wherein $C_{3-12}$ aryl may be phenyl or naphthalenyl; and wherein $C_{3-12}$ heteroaryl may be furanyl, thiophenyl, pyridinyl, pyrrolyl, imidazolyl, or pyrimidinyl.

In another exemplary embodiment, $R_1$ and $R_2$ may be taken together with nitrogen to which they are attached to form $C_{3-6}$ heterocycloalkyl selected from the group consisting of azetidinyl, pyrrolidinyl, piperidinyl, morpholinyl, piperazinyl, and azepanyl; or $C_{3-6}$ heterocycloalkene selected from the group consisting of dihydroazetinyl, dihydropyrrolinyl, dihydropyridinyl, and tetrahydropyridinyl; and $R_3$ may be H; $C_{4-2}$ cycloalkyl; $C_{3-12}$ aryl; or $C_{1-4}$ alkyl unsubstituted or substituted with $C_{3-12}$ aryl or $C_{3-12}$ heteroaryl;

wherein $C_{3-8}$ heterocycloalkyl, $C_{3-7}$ cycloalkyl, $C_{3-12}$ aryl, or $C_{3-12}$ heteroaryl may be unsubstituted or substituted with at least one non-hydrogen substituent selected from the group consisting of halogen, $C_{1-4}$ alkyl, and $C_{1-4}$ alkoxy, and the non-hydrogen substituent may be unsubstituted or further substituted with halogen.

In still another exemplary embodiment, $R_1$ and $R_2$ may be taken together with nitrogen to which they are attached to form $C_{3-6}$ heterocycloalkyl selected from the group consisting of azetidinyl, pyrrolidinyl, piperidinyl, morpholinyl, piperazinyl, and azepanyl; or $C_{3-6}$ heterocycloalkene selected from the group consisting of dihydroazetinyl, dihydropyrrolinyl, dihydropyridinyl, and tetrahydropyridinyl; and $R_3$ may be H; $C_{4-7}$ cycloalkyl; $C_{3-12}$ aryl selected from phenyl and naphthalenyl; $C_{1-4}$ alkyl unsubstituted or substituted with $C_{3-12}$ aryl or $C_{3-12}$ heteroaryl selected from the group consisting of phenyl, naphthalenyl, furanyl, thiophenyl, pyridinyl, pyrrolyl, and imidazolyl;

wherein $C_{3-12}$ aryl or $C_{3-12}$ heteroaryl may be unsubstituted or substituted with at least one non-hydrogen substituent selected from the group consisting of halogen, $C_{3-4}$ alkyl, and $C_{1-4}$ alkoxy, and the non-hydrogen substituent may be unsubstituted or further substituted with halogen.

In still another exemplary embodiment, $R_1$ and $R_2$ may be taken together with nitrogen to which they are attached to form $C_{3-6}$ heterocycloalkyl selected from the group consisting of azetidinyl, pyrrolidinyl, piperidinyl, and azepanyl; and $R_3$ may be $C_{5-7}$ cycloalkyl; phenyl; or $C_{1-2}$ alkyl unsubstituted or substituted with phenyl or thiophenyl;

wherein phenyl may be unsubstituted or substituted with at least one non-hydrogen substituent selected from the group consisting of halogen, $C_{1-4}$ alkyl, and $C_{1-4}$ alkoxy, and the non-hydrogen substituent may be unsubstituted or further substituted with halogen.

In still another exemplary embodiment, $R_1$ and $R_2$ may be taken together with nitrogen to which they are attached to form $C_{3-6}$ heterocycloalkyl selected from the group consisting of azetidinyl, pyrrolidinyl, piperidinyl, and azepanyl; and $R_3$ may be phenyl unsubstituted or substituted with at least one non-hydrogen substituent selected from the group consisting of halogen, $C_{1-2}$ alkyl, and $C_{1-2}$ alkoxy, and the non-hydrogen substituent may be unsubstituted or further substituted with halogen.

In still another exemplary embodiment, $R_1$ and $R_2$ may be taken together with nitrogen to which they are attached to form $C_{3-6}$ heterocycloalkyl selected from the group consisting of azetidinyl, pyrrolidinyl, piperidinyl, and azepanyl; and $R_3$ may be $C_{1-2}$ alkyl substituted with phenyl or thiophenyl, wherein phenyl may be unsubstituted or substituted with at least one non-hydrogen substituent selected from the group consisting of halogen, $C_{1-2}$ alkyl, and $C_{1-2}$ alkoxy, and the non-hydrogen substituent may be unsubstituted or further substituted with halogen.

In still another exemplary embodiment, $R_1$ and $R_2$ may be taken together with nitrogen to which they are attached to form $C_{3-6}$ heterocycloalkyl selected from the group consisting of azetidinyl, pyrrolidinyl, piperidinyl, and azepanyl; and $R_3$ may be $C_{6-7}$ cycloalkyl or unsubstituted $C_{1-2}$ alkyl.

In still another exemplary embodiment, $R_1$ and $R_2$ may be taken together with nitrogen to which they are attached to form $C_{3-6}$ heterocycloalkyl selected from the group consisting of azetidinyl, pyrrolidinyl, piperidinyl, and azepanyl; and $R_3$ may be cyclohexyl, cycloheptyl, phenyl, benzyl, phenethyl, thiophenylethyl, or methyl, wherein phenyl, benzyl, or phenethyl may be unsubstituted or substituted with at least one non-hydrogen substituent selected from the group consisting of halogen, methyl, ethyl, methoxy, trifluoromethyl, difluoromethoxy, and trifluoromethoxy.

In still another exemplary embodiment, $R_1$ and $R_2$ may be taken together with nitrogen to which they are attached to form $C_{3-6}$ heterocycloalkene selected from the group consisting of dihydroazetinyl, dihydropyrrolinyl, dihydropyridinyl, and tetrahydropyridinyl; and $R_3$ may be H; $C_{1-6}$ alkyl; phenyl; or $C_{1-4}$ alkyl substituted with phenyl;

wherein $C_{3-6}$ heterocycloalkene is unsubstituted or substituted with $C_{1-6}$ alkyl, and phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

In still another exemplary embodiment, $R_1$ and $R_2$ may be taken together with nitrogen to which they are attached to form dihydropyrrolinyl or tetrahydropyridinyl unsubstituted or substituted with $C_{1-4}$ alkyl; and $R_3$ may be H; $C_{1-6}$ alkyl; phenyl; or $C_{1-4}$ alkyl substituted with phenyl;

wherein phenyl may be unsubstituted or substituted with at least one non-hydrogen substituent selected from the group consisting of halogen, $C_{1-4}$ alkoxy, haloalkyl, and $C_{1-4}$ haloalkoxy.

In still another exemplary embodiment, $R_1$ and $R_2$ may be taken together with nitrogen to which they are attached to form 5- to 6-membered $C_{4-6}$ heterocloalkene; and $R_3$ may be H; $C_{1-6}$ alkyl; phenyl; or $C_{1-2}$ alkyl substituted with phenyl;

wherein $C_{4-5}$ heterocycloalkene may be unsubstituted or substituted with $C_{1-2}$ alkyl; and phenyl may be unsubstituted or substituted with at least one non-hydrogen substituent selected from the group consisting of halogen, $C_{1-2}$ alkoxy, $C_{1-2}$ haloalkyl, and $C_{1-2}$ haloalkoxy.

In still another exemplary embodiment, $R_1$ and $R_2$ may be taken together with nitrogen to which they are attached to form dihydropyrrolinyl or tetrahydropyridinyl unsubstituted or substituted with $C_{1-2}$ alkyl; and $R_3$ may be H; $C_{3-6}$ alkyl; phenyl; or $C_{1-2}$ alkyl substituted with phenyl;

wherein phenyl may be unsubstituted or substituted with at least one non-hydrogen substituent selected from the group consisting of halogen, $C_{1-2}$ alkoxy, $C_{1-2}$ haloalkyl, and $C_{1-2}$ haloalkoxy.

In still another exemplary embodiment, $R_1$ and $R_2$ may be taken together with nitrogen to which they are attached to form dihydropyrrolinyl or tetrahydropyridinyl unsubstituted or substituted with methyl; and $R_3$ may be H; butyl; propyl; hexyl; phenyl; or methyl substituted with phenyl;

wherein phenyl may be unsubstituted or substituted with at least one non-hydrogen substituent selected from the group consisting of halogen, methoxy, trihaloalkyl, and trihalomethoxy.

In still another exemplary embodiment, $R_1$ and $R_2$ may be taken together with nitrogen to which they are attached to form $C_{3-6}$ heterocycloalkyl selected from the group consisting of azetidinyl, piperidinyl, and pyrrolidinyl; and $R_3$ may be phenyl; or $C_{1-4}$ alkyl substituted with phenyl;

wherein $C_{3-6}$ heterocycloalkyl may be substituted with one to four $C_{1-6}$ alkyl, and phenyl may be unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

In still another exemplary embodiment, $R_1$ and $R_2$ may be taken together with nitrogen to which they are attached to form piperidinyl or pyrrolidinyl; and $R_3$ may be phenyl; or $C_{1-4}$ alkyl substituted with phenyl;

wherein $C_{3-6}$ heterocycloalkyl may be substituted with $C_{1-4}$ alkyl in at least one of positions of 2, 3, 5, and 6, and phenyl may be unsubstituted or substituted with at least one non-hydrogen substituent selected from the group consisting of halogen, $C_{1-4}$ haloalkyl, and $C_{1-4}$ haloalkoxy.

In still another exemplary embodiment, $R_1$ and $R_2$ may be taken together with nitrogen to which they are attached to form 5- to 6-membered $C_{4-5}$ heterocloalkyl; and $R_3$ may be phenyl; or $C_{1-2}$ alkyl substituted with phenyl;

wherein C$_{4-5}$ heterocycloalkyl may be substituted with one or two C$_{1-2}$ alkyl, and phenyl may be unsubstituted or substituted with at least one non-hydrogen substituent selected from the group consisting of halogen, C$_{1-2}$ haloalkyl, and C$_{1-2}$ haloalkoxy.

In still another exemplary embodiment,

R$_1$ and R$_2$ may be taken together with nitrogen to which they are attached to form piperidinyl or pyrrolidinyl substituted with one or two C$_{1-2}$ alkyl; and R$_3$ may be phenyl; or C$_{1-2}$ alkyl substituted with phenyl;

wherein phenyl may be unsubstituted or substituted with at least one non-hydrogen substituent selected from the group consisting of halogen, C$_{1-2}$ haloalkyl, and C$_{1-2}$ haloalkoxy.

In still another exemplary embodiment,

R$_1$ and R$_2$ may be taken together with nitrogen to which they are attached to form piperidinyl or pyrrolidinyl; and R$_3$ may be phenyl; or C$_{1-2}$ alkyl substituted with phenyl;

wherein piperidinyl or pyrrolidinyl may be substituted with one or two C$_{1-2}$ alkyl in at least one of positions of 2, 3, 5, and 6, and phenyl is unsubstituted or substituted with at least one non-hydrogen substituent selected from the group consisting of halogen, C$_{1-2}$ haloalkyl, and C$_{1-2}$ haloalkoxy.

In still another exemplary embodiment,

R$_1$ and R$_2$ may be taken together with nitrogen to which they are attached to form piperidine; and R$_3$ may be phenyl; or methyl substituted with phenyl;

wherein piperidine may be substituted with one or two methyl in at least one of positions of 2, 3, 5, and 6, and phenyl is unsubstituted or substituted with at least one non-hydrogen substituent selected from the group consisting of halogen, trihalomethyl, and trihalomethoxy.

In still another exemplary embodiment, the compound of Formula 1 may be:

N1-piperidine-N5-phenyl biguanide;
N1-piperidine-N5-(3-methyl)phenyl biguanide;
N1-piperidine-N5-(3-ethyl)phenyl biguanide;
N1-piperidine-N5-(3-methoxy)phenyl biguanide;
N1-piperidine-N5-(4-fluoro)phenyl biguanide;
N1-piperidine-N5-(3-fluoro)phenyl biguanide;
N1-pyrrolidine-N5-(4-chloro)phenyl biguanide;
N1-piperidine-N5-(4-chloro)phenyl biguanide;
N1-piperidine-N5-(3-bromo)phenyl biguanide;
N1-pyrrolidine-N5-(3-chloro)phenyl biguanide;
N1-piperidine-N5-(3-chloro)phenyl biguanide;
N1-azepane-N5-(3-chloro)phenyl biguanide;
N1-pyrrolidine-N5-(3-trifluoromethyl)phenyl biguanide;
N1-piperidine-N5-(3-trifluoromethyl)phenyl biguanide;
N1-pyrrolidine-N5-(4-trifluoromethyl)phenyl biguanide;
N1-piperidine-N5-(4-trifluoromethyl)phenyl biguanide;
N1-pyrrolidine-N5-(3-trifluoromethoxy)phenyl biguanide;
N1-piperidine-N5-(3-trifluoromethoxy)phenyl biguanide;
N1-piperidine-N5-(3-difluoromethoxy)phenyl biguanide;
N1-pyrrolidine-N5-(4-trifluoromethoxy)phenyl biguanide;
N1-piperidine-N5-(4-trifluoromethoxy)phenyl biguanide;
N1-piperidine-N5-(4-fluoro-3-trifluoromethyl)phenyl biguanide;
N1-piperidine-N5-(4-chloro-3-trifluoromethyl)phenyl biguanide;
N1-pyrrolidine-N5-(3-fluoro-4-trifluoromethyl)phenyl biguanide;
N1-piperidine-N5-(3-fluoro-4-trifluoromethyl)phenyl biguanide;
N1-piperidine-N5-(4-chloro-3-trifluoromethoxy)phenyl biguanide;
N1-azetidine-N5-(3-fluoro-4-trifluoromethoxy)phenyl biguanide;
N1-pyrrolidine-N5-(3-fluoro-4-trifluoromethoxy)phenyl biguanide;
N1-piperidine-N5-(3-fluoro-4-trifluoromethoxy)phenyl biguanide;
N1-azetidine-N5-(3-chloro-4-trifluoromethoxy)phenyl biguanide;
N1-pyrrolidine-N5-(3-chloro-4-trifluoromethoxy)phenyl biguanide;
N1-piperidine-N5-(3-chloro-4-trifluoromethoxy)phenyl biguanide;
N1-piperidine-N5-(3,4-difluoro)phenyl biguanide;
N1-piperidine-N5-(3,5-difluoro)phenyl biguanide;
N1-piperidine-N5-(3,5-dichloro)phenyl biguanide;
N1-pyrrolidine-N5-(3,4-dichloro)phenyl biguanide;
N1-piperidine-N5-(3,4-dichloro)phenyl biguanide;
N1-piperidine-N5-(3-chloro-5-trifluoromethoxy)phenyl biguanide;
N1-pyrrolidine-N5-(3-bromo-5-trifluoromethoxy)phenyl biguanide;
N1-piperidine-N5-(3-bromo-5-trifluoromethoxy)phenyl biguanide;
N1-piperidine-N5-(3,4,5-trifluoro)phenyl biguanide;
N1-pyrrolidine-N5-(4-trifluoromethyl)phenyl biguanide;
N1-piperidine-N5-(4-trifluoromethyl)phenyl biguanide;
N1-pyrrolidine-N5-(4-trifluoromethoxy)phenyl biguanide;
N1-piperidine-N5-(4-trifluoromethoxy)phenyl biguanide;
N1-pyrrolidine-N5-(3-fluoro-4-trifluoromethyl)phenyl biguanide;
N1-piperidine-N5-(3-fluoro-4-trifluoromethyl)phenyl biguanide;
N1-pyrrolidine-N5-(3-fluoro-4-trifluoromethoxy)phenyl biguanide;
N1-piperidin-N5-(3-fluoro-4-trifluoromethoxy)phenyl biguanide;
N1-piperidine-N5-(3-trifluoromethyl)benzyl biguanide;
N1-piperidine-N5-methyl biguanide;
N1-piperidine-N5-cyclohexyl biguanide;
N1-pyrrolidine-N5-cycloheptyl biguanide;
N1-piperidine-N5-cycloheptyl biguanide;
N1-azepane-N5-cycloheptyl biguanide;
N1-piperidine-N5-(4-methyl)benzyl biguanide;
N1-piperidine-N5-(4-methoxy)benzyl biguanide;
N1-pyrrolidine-N5-(4-chloro)benzyl biguanide;
N1-azepane-N5-(4-chloro)benzyl biguanide;
N1-piperidine-N5-(4-trifluoromethyl)benzyl biguanide;
N1-azetidine-N5-(4-trifluoromethoxy)benzyl biguanide;
N1-pyrrolidine-N5-(4-trifluoromethoxy)benzyl biguanide;
N1-piperidine-N5-(4-trifluoromethoxy)benzyl biguanide;
N1-piperidine-N5-(4-fluoro-3-trifluoromethyl)benzyl biguanide;
N1-piperidine-N5-(4-chloro-3-trifluoromethyl)benzyl biguanide;
N1-piperidine-N5-(3-fluoro-4-trifluoromethyl)benzyl biguanide;
N1-piperidine-N5-(3-chloro-4-trifluoromethyl)benzyl biguanide;
N1-piperidine-N5-(4-fluoro-3-trifluoromethoxy)benzyl biguanide;
N1-piperidine-N5-(3-chloro-4-trifluoromethoxy)benzyl biguanide;
N1-piperidine-N5-(2,6-difluoro)benzyl biguanide;
N1-piperidine-N5-(3,4-difluoro)benzyl biguanide;
N1-piperidine-N5-(2,4-dichloro)benzyl biguanide;
N1-pyrrolidine-N5-(3,4-dichloro)benzyl biguanide;
N1-piperidine-N5-(3,4-dichloro)benzyl biguanide;

N1-piperidine-N5-(thiophen-2-yl)ethyl biguanide;
N1-pyrrolidine-N5-(phenethyl) biguanide;
N1-piperidine-N5-(phenethyl) biguanide;
N1-azepane-N5-(phenethyl) biguanide;
N1-azepane-N5-(3-fluoro)phenethyl) biguanide,
N1-azepane-N5-(4-chloro)phenethyl) biguanide;
N1-1,2-dihydropyrrole-N5-(4-trifluoromethoxy)phenyl biguanide;
N1-1,2-dihydropyrrole-N5-(4-trifluoromethyl)phenyl biguanide;
N1-1,2-dihydropyrrole-N5-(3-trifluoromethyl)phenyl biguanide;
N1-1,2-dihydropyrrole-N5-(4-fluoro)phenyl biguanide;
N1-1,2-dihydropyrrole-N5-(4-chloro)phenyl biguanide;
N1-1,2-dihydropyrrole-N5-(4-bromo)phenyl biguanide;
N1-1,2-dihydropyrrole-N5-(3-chloro, 4-trifluoromethoxy)phenyl biguanide;
N1-1,2,3,6-tetrahydropyridine-N5-(3-chloro, 4-trifluoromethoxy)phenyl biguanide;
N1-1,2-dihydropyrrole-N5-(3-trifluoromethyl)benzyl biguanide;
N1-1,2-dihydropyrrole-N5-(4-trifluoromethyl)benzyl biguanide;
N1-1,2-dihydropyrrole-N5-(3-trifluoromethoxy)benzyl biguanide;
N1-(3-methyl)-1,2-dihydropyrrole-N5-(4-trifluoromethoxy)phenyl biguanide;
N1-(3-methyl)-1,2-dihydropyrrole-N5-(4-trifluoromethyl)phenyl biguanide;
N1-(3-methyl)-1,2-dihydropyrrole-N5-(4-chloro)phenyl biguanide;
N1-(3-methyl)-1,2-dihydropyrrole-N5-(4-chloro, 3-trifluoromethyl)phenyl biguanide;
N1-(3-methyl)-1,2-dihydropyrrole-N5-(3-trifluoromethyl)phenyl biguanide;
N1-(3-methyl)-1,2-dihydropyrrole-N5-(4-fluoro)phenyl biguanide;
N1-(3-methyl)-1,2-dihydropyrrole-N5-(4-bromo)phenyl biguanide;
N1-(3-methyl)-1,2-dihydropyrrole-N5-(4-methoxy)phenyl biguanide;
N1-(3-methyl)-1,2-dihydropyrrole-N5-(3,4-dimethoxy)phenyl biguanide;
N1-(3-methyl)-1,2-dihydropyrrole-N5-(4-trifluoromethoxy)benzyl biguanide;
N1-(3-methyl)-1,2-dihydropyrrole-N5-(3-trifluoromethoxy)phenyl biguanide;
N1-(3-methyl)-1,2-dihydropyrrole-N5-(4-trifluoromethyl)benzyl biguanide;
N1-(3-methyl)-1,2-dihydropyrrole-N5-(4-chloro, 3-trifluoromethyl)benzyl biguanide;
N1-1,2,3,6-tetrahydropyridine-N5-(4-trifluoromethoxy)phenyl biguanide;
N1-1,2,3,6-tetrahydropyridine-N5-(4-trifluoromethyl)phenyl biguanide;
N1-1,2,3,6-tetrahydropyridine-N5-(3-trifluoromethoxy)phenyl biguanide;
N1-1,2,3,6-tetrahydropyridine-N5-(3-trifluoromethyl)phenyl biguanide;
N1-1,2,3,6-tetrahydropyridine-N5-(4-fluoro, 3-trifluoromethyl)phenyl biguanide;
N1-1,2,3,6-tetrahydropyridine-N5-(4-chloro, 3-trifluoromethoxy)phenyl biguanide;
N1-1,2,3,6-tetrahydropyridine-N5-(3-fluoro,4-trifluoromethoxy)phenyl biguanide;
N1-1,2,3,6-tetrahydropyridine-N5-(4-chloro)phenyl biguanide;
N1-1,2,3,6-tetrahydropyridine-N5-(4-bromo)phenyl biguanide;
N1-1,2,3,6-tetrahydropyridine-N5-(4-fluoro)phenyl biguanide;
N1-1,2,3,6-tetrahydropyridine-N5-(3,5-dimethoxy)phenyl biguanide;
N1-1,2,3,6-tetrahydropyridine-N5-phenyl biguanide;
N1-1,2,3,6-tetrahydropyridine-N5-(4-methoxy)phenyl biguanide;
N1-1,2,3,6-tetrahydropyridine-N5-(3-methoxy)phenyl biguanide;
N1-1,2-dihydropyrrole-N5-(4-methoxy)phenyl biguanide;
N1-1,2-dihydropyrrole-N5-(3-methoxy)phenyl biguanide;
N1-1,2-dihydropyrrole-N5-phenyl biguanide;
N1-1,2-dihydropyrrole-N5-(3,5-dimethoxy)phenyl biguanide;
N1-1,2-dihydropyrrole-N5-(4-fluoro, 3-trifluoromethyl)phenyl biguanide;
N1-1,2-dihydropyrrole-N5-(3-fluoro, 4-trifluoromethyl)phenyl biguanide;
N1-1,2,3,6-tetrahydropyridine-N5-(4-methyl)phenyl biguanide;
N1-1,2,3,6-tetrahydropyridine-N5-(3-methyl)phenyl biguanide;
N1-1,2-dihydropyrrole-N5-(4-methyl)phenylbiguanide;
N1-1,2-dihydropyrrole-N5-(3-methyl)phenyl biguanide;
N1-1,2-dihydropyrrole-N5-(3-trifluoromethoxy)phenyl biguanide;
N1-1,2,3,6-tetrahydropyridine-N5-hexyl biguanide;
N1-1,2,3,6-tetrahydropyridine-N5-(4-trifluoromethoxy)benzyl biguanide;
N1-1,2,3,6-tetrahydropyridine-N5-(3-trifluoromethoxy)benzyl biguanide;
N1-1,2,3,6-tetrahydropyridine-N5-(4-trifluoromethyl)benzyl biguanide;
N1-1,2,3,6-tetrahydropyridine-N5-(3-trifluoromethyl)benzyl biguanide;
N1-1,2,3,6-tetrahydropyridine-N5-(4-chloro, 3-trifluoromethyl)benzyl biguanide;
N1-1,2,3,6-tetrahydropyridine-N5-butyl biguanide;
N1-1,2,3,6-tetrahydropyridine-N5-propyl biguanide;
N1-1,2,3,6-tetrahydropyridine biguanide;
N1-(3-methyl)piperidine-N5-(3-trifluoromethyl)benzyl biguanide;
N1-(3-methyl)piperidine-N5-(4-chloro)benzyl biguanide;
N1-(3-methyl)piperidine-N5-(4-fluoro)phenyl biguanide;
N1-(3-methyl)piperidine-N5-(4-bromo)phenyl biguanide;
N1-(3-methyl)piperidine-N5-(4-chloro, 3-trifluoromethyl)phenyl biguanide;
N1-(3-methyl)piperidine-N5-(3-fluoro, 4-trifluoromethyl)phenyl biguanide;
N1-(3-methyl)piperidine-N5-(4-fluoro, 3-trifluoromethyl)phenyl biguanide;
N1-(2-methyl)piperidine-N5-(4-trifluoromethoxy)phenyl biguanide;
N1-(2-methyl)piperidine-N5-(3-trifluoromethoxy)phenyl biguanide;
N1-(2-methyl)piperidine-N5-(4-trifluoromethyl)phenyl biguanide;
N1-(3-methyl)piperidine-N5-(3-fluoro, 4-trifluoromethoxy)phenyl biguanide;
N1-(2-methyl)piperidine-N5-(3-fluoro, 4-trifluoromethoxy)phenyl biguanide;
N1-(2-methyl)piperidine-N5-(4-chloro)phenyl biguanide;
N1-(2-methyl)piperidine-N5-(4-fluoro, 3-trifluoromethyl)phenyl biguanide;

N1-(2-methyl)piperidine-N5-(3-trifluoromethyl)phenyl biguanide;
N1-(2-methyl)piperidine-N5-(4-chloro, 3-trifluoromethyl)phenyl biguanide;
N1-(3-methyl)piperidine-N5-(4-trifluoromethyl)phenyl biguanide;
N1-(3-methyl)piperidine-N5-(4-trifluoromethoxy)phenyl biguanide;
N1-(3-methyl)piperidine-N5-(3-trifluoromethoxy)phenyl biguanide;
N1-(3-methyl)piperidine-N5-(4-trifluoromethoxy)benzyl biguanide;
N1-(3-methyl)piperidine-N5-(4-fluoro, 3-trifluoromethyl)phenyl biguanide;
N1-(3-methyl)piperidine-N5-(4-trifluoromethyl)benzyl biguanide;
N1-(3-methyl)piperidine-N5-(4-chloro)phenyl biguanide;
N1-(3-methyl)piperidine-N5-(3-trifluoromethyl)phenyl biguanide;
N1-(2,6-dimethyl)piperidine-N5-(4-trifluoromethoxy)phenyl biguanide;
N1-(2,6-dimethyl)piperidine-N5-(3-trifluoromethoxy)phenyl biguanide;
N1-(2,6-dimethyl)piperidine-N5-(4-trifluoromethyl)phenyl biguanide;
N1-(2,6-dimethyl)piperidine-N5-(3-trifluoromethyl)phenyl biguanide;
N1-(2,6-dimethyl)piperidine-N5-(4-fluoro, 3-trifluoromethyl)phenyl biguanide;
N1-(2,6-dimethyl)piperidine-N5-(4-chloro, 3-trifluoromethyl)phenyl biguanide;
N1-(2,6-dimethyl)piperidine-N5-(3-fluoro, 4-trifluoromethoxy)phenyl biguanide;
N1-(2,6-dimethyl)piperidine-N5-(4-chloro)phenyl biguanide;
N1-(2,6-dimethyl)piperidine-N5-(4-bromo)phenyl biguanide; or
N1-(2,6-dimethyl)piperidine-N5-(4-fluoro)phenyl biguanide.

In particular, the pharmaceutically acceptable salt of Formula 1 according to the present invention may be an acid addition salt formed using an organic or inorganic acid. Examples of the organic acid may include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxyacetic acid, benzenesulfonic acid, 4-toluenesulfonic acid, and methanesulfonic acid. Examples of the inorganic acid may include hydrochloric acid, bromic acid, sulfuric acid, phosphoric acid, nitric acid, carbonic acid, and boric acid.

The acid addition salt mentioned above may be prepared by the conventional methods of salt preparation, for example, by a) directly mixing the compound of Formula 1 with an acid, b) mixing any of these by dissolving in a solvent or water-containing solvent, or c) mixing the compound of Formula 1 with an acid in the presence of a solvent or hydrated solvent.

In an exemplary embodiment, the pharmaceutically acceptable salt of the compound of Formula 1 may be a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methanesulfonic acid, dichloroacetic acid, aminooxyacetic acid, hydrochloric acid, bromic acid, sulfuric acid, phosphoric acid, nitric acid, carbonic acid, and boric acid.

The compound of Formula 1 and a pharmaceutically acceptable salt thereof may be effectively used for preventing or treating fibrosis by the excellent EMT-suppressing effect through inhibition of Snail, which is an EMT-related transcription factor, as can be confirmed in Examples below.

Accordingly, the present invention provides a pharmaceutical composition for preventing or treating fibrosis containing a compound of Formula 1 above or a pharmaceutically acceptable salt thereof as an active ingredient; a use of the compound of Formula 1 or a pharmaceutically acceptable salt thereof in preparing a medicine for preventing or treating fibrosis; and a method for preventing or treating fibrosis including administering a therapeutically effective amount of the compound of Formula 1 above or a pharmaceutically acceptable salt thereof to a subject in need thereof.

The fibrosis may be selected from the group consisting of liver fibrosis (alcoholic, viral, autoimmune, metabolic, and genetic chronic disease), renal fibrosis (e.g., caused by chronic inflammation, infection, or type II diabetes mellitus), pulmonary fibrosis (caused by environmental contamination including toxic particles, sarcoidosis, asbestosis, bacterial infection including hypersensitivity pneumonitis and tuberculosis, cystic fibrosis, lung transplantation, and drugs), interstitial fibrosis, systemic scleroderma (autoimmune disease where many organs become fibrotic), macular degeneration (disease of ocular fibrosis), pancreatic fibrosis (e.g., caused by alcohol abuse and chronic inflammatory disease in pancreas), spleen fibrosis (caused by sickle-cell anemia and other vascular diseases), cardiac fibrosis (caused by inflammations, infections, and hypertrophy), mediastinal fibrosis, myelofibrosis, vascular fibrosis, skin fibrosis, ocular fibrosis, arthrofibrosis, muscle fibrosis, thyroid fibrosis, endomyocardial fibrosis, peritoneal fibrosis, retroperitoneal fibrosis, progressive massive fibrosis, nephrogenic systemic fibrosis, post-operative fibrotic complication, in particular, fibrotic complication by surgical implant, and infection-associated fibrosis.

The pharmaceutical composition of the present invention may include at least one pharmaceutically acceptable carrier, in addition to active ingredients. As used herein, the "pharmaceutically acceptable carrier" refers to a pharmaceutical excipient, which is used in formulating pharmaceutically active compounds for administration and known as non-toxic and non-sensitive under the conditions of usage.

The exact ratio of the excipient may be determined not only by the solubility, chemical properties, selected route of administration of an active compound, but also by the standard pharmaceutical practices.

The pharmaceutical composition of the present invention may be formulated into a form suitable for the desired administration, using additives such as an appropriate and physiologically acceptable excipient, a disintegrant, a sweetener, a binder, a coating agent, an extender, a swelling agent, a lubricant, a glidant, a flavoring agent, etc.

The pharmaceutical composition may be formulated into tablets, capsules, pills, granules, powders, injections, and liquids, although it is not limited thereto.

The formulations of the pharmaceutical composition and pharmaceutically acceptable carriers may be appropriately selected according to the technologies known in the art, for example, according to the following references: [Urquhart et al., Lancet, 16:367, 1980]; [Lieberman et al., PHARMACEUTICAL DOSAGE FORMS-DISPERSE SYSTEMS, 2nd ed., vol. 3, 1998]; [Ansel et al., PHARMACEUTICAL DOSAGE FORMS & DRUG DELIVERY SYSTEMS, 7th ed., 2000]; [Martindale, THE EXTRA PHARMACOPEIA, 31st ed.]; [Remington's PHARMACEUTICAL SCIENCES, 16th-20th editions]; [THE PHARMACOLOGICAL BASIS OF THERAPEUTICS, Goodman and Gilman, eds., 9th ed., 1996]; [Wilson and Gisvolds' TEXTBOOK OF ORGANIC MEDICINAL AND PHARMACEUTICAL CHEMISTRY, Delgado and Remers, eds., 10th ed., 1998]. Additionally, the principle of formulating a pharmaceutical composition may be referred, for example, to the following references [Platt, Clin Lab Med, 7: 289-99, 1987]; [Aulton, PHARMACEUTICS: THE SCIENCE OF DOSAGE FORM DESIGN, Churchill Livingstone, N.Y., 1988]; [EXTEMPORANEOUS ORAL LIQUID DOSAGE PREPARATIONS, CSHP, 1998], ["Drug Dosage" J Kans Med Soc, 70(1): 30-32, 1969], etc.

As used herein, the term "treatment" refers to any action to alleviate symptoms, to temporarily or permanently eliminate the cause(s) of symptoms, to prevent or delay of the occurrence of symptoms and the progress of the diseases, disorders, and illnesses described above, but it is not limited thereto.

As used herein, the term "effective dose" of an active ingredient of the pharmaceutical composition of the present invention refers to the amount required for completing treatment of a given disease. Accordingly, the effective dose may be adjusted according to various factors including the type of a disease, severity of illness, active ingredients contained in a composition and kinds and contents of other ingredients contained therein, formulation type, age, weight, health status, sex, and diets of a patient, duration and route of administration, release rate of a composition, length of treatment, and drugs used in combination. For adults, for example, the compound of Formula 1 may be administered once or a few times daily, in the amount of a total of from 50 mg/kg to 3000 mg/kg.

Advantageous Effects of the Invention

The compound of Formula 1 or a pharmaceutically acceptable salt thereof may be used for preventing and treating fibrosis by effectively suppressing the EMT action.

BRIEF DESCRIPTION OF THE DRAWINGS

FIG. 1 shows the inhibitory effect of a biguanide derivative of Formula 1 against the expression of Snail, which is an EMT-related transcription factor.

FIG. 2 shows the normalization of the thickness of thickened peritoneum in a peritoneal fibrosis model by a biguanide derivative of Formula 1.

FIG. 3 shows graphs illustrating the scaled thickness of peritonea according to treatment by a biguanide derivative of Formula 1.

FIG. 4 shows the expression levels of EMT-related transcription factors in peritoneal mesothelial cells by a biguanide derivative of Formula 1.

FIG. 5 shows the level of morphological changes in peritoneal mesothelial cells by a biguanide derivative of Formula 1.

DETAILED DESCRIPTION OF THE PREFERRED EMBODIMENTS

The advantages and features of the present invention and the methods to achieve them will become more clear from the exemplary embodiments described herein below. However, it is to be understood that the present invention should not be limited to these exemplary embodiments but can be embodied in many different forms, and that the specific technical features are merely provided for illustrative purposes so that one of ordinary skill in the art can fully understand the scope of the present invention, and thus the substantial scope of the present invention shall be defined in the appended claims and their equivalents.

Examples

The following compounds synthesized by the methods described in Korean Patent Application Publication Nos. 10-2012-0086996, 10-2012-0086999, 10-2013-0014175, and 10-2013-0014176 were evaluated regarding their effects of suppressing EMT actions and therapeutic effects in a model with peritoneal fibrosis, according to the methods described in Experimental Examples shown below.

TABLE 1

| Example | Compound |
|---|---|
| 1 | N1-piperidine-N5-phenyl biguanide hydrochloride [N-(N-phenylcarbamimidoyl)piperidine-1-carboximidamidehydrochloride] |
| 2 | N1-piperidine-N5-(3-methyl)phenyl biguanide hydrochloride [N-(N-m-tolylcarbamimidoyl)piperidine-1-carboximidamidehydrochloride] |
| 3 | N1-piperidine-N5-(3-ethyl)phenyl biguanide hydrochloride [N-(N-(3-ethylphenyl)carbamimidoyl)piperidine-1-carboximidamidehydrochloride] |
| 4 | N1-piperidine-N5-(3-methoxy)phenyl biguanide hydrochloride [N-(N-(3-methoxyphenyl)carbamimidoyl)piperidine-1-carboximidamidehydrochloride] |
| 5 | N1-piperidine-N5-(4-fluoro)phenyl biguanide hydrochloride [N-(N-(4-fluorophenyl)carbamimidoyl)piperidine-1-carboximidamidehydrochloride] |
| 6 | N1-piperidine-N5-(3-fluoro)phenyl biguanide hydrochloride [N-(N-(3-fluorophenyl)carbamimidoyl)piperidine-1-carboximidamidehydrochloride] |
| 7 | N1-pyrrolidine-N5-(4-chloro)phenyl biguanide hydrochloride [N-(N-(4-chlorophenyl)carbamimidoyl)pyrrolidine-1-carboximidamidehydrochloride] |

TABLE 1-continued

| Example | Compound |
|---|---|
| 8 | N1-piperidine-N5-(4-chloro)phenyl biguanide hydrochloride [N-(N-(4-chlorophenyl)carbamimidoyl)piperidine-1-carboximidamidehydrochloride] |
| 9 | N1-piperidine-N5-(3-bromo)phenyl biguanide hydrochloride [N-(N-(3-bromophenyl)carbamimidoyl)piperidine-1-carboximidamidehydrochloride] |
| 10 | N1-pyrrolidine-N5-(3-chloro)phenyl biguanide hydrochloride [N-(N-(3-chlorophenyl)carbamimidoyl)pyrrolidine-1-carboximidamidehydrochloride] |
| 11 | N1-piperidine-N5-(3-chloro)phenyl biguanide hydrochloride [N-(N-(3-chlorophenyl)carbamimidoyl)piperidine-1-carboximidamidehydrochloride] |
| 12 | N1-azepane-N5-(3-chloro)phenyl biguanide hydrochloride [N-(N-(3-chlorophenyl)carbamimidoyl)azepane-1-carboximidamidehydrochloride] |
| 13 | N1-pyrrolidine-N5-(3-trifluoromethyl)phenyl biguanide hydrochloride [N-(N-(3-(trifluoromethyl)phenyl)carbamimidoyl)pyrrolidine-1-carboximidamidehydrochloride] |
| 14 | N1-piperidine-N5-(3-trifluoromethyl)phenyl biguanide hydrochloride [N-(N-(3-(trifluoromethyl)phenyl)carbamimidoyl)piperidine-1-carboximidamidehydrochloride] |
| 15 | N1-pyrrolidine-N5-(4-trifluoromethyl)phenyl biguanide hydrochloride [N-(N-(4-(trifluoromethyl)phenyl)carbamimidoyl)pyrrolidine-1-carboximidamidehydrochloride] |
| 16 | N1-piperidine-N5-(4-trifluoromethyl)phenyl biguanide hydrochloride [N-(N-(4-(trifluoromethyl)phenyl)carbamimidoyl)piperidine-1-carboximidamidehydrochloride] |
| 17 | N1-pyrrolidine-N5-(3-trifluoromethoxy)phenyl biguanide hydrochloride [N-(N-(3-(trifluoromethoxy)phenyl)carbamimidoyl)pyrrolidine-1-carboximidamidehydrochloride] |
| 18 | N1-piperidine-N5-(3-trifluoromethoxy)phenyl biguanide hydrochloride [N-(N-(3-(trifluoromethoxy)phenyl)carbamimidoyl)piperidine-1-carboximidamidehydrochloride] |
| 19 | N1-piperidine-N5-(3-difluoromethoxy)phenyl biguanide hydrochloride [N-(N-(3-(difluoromethoxy)phenyl)carbamimidoyl)piperidine-1-carboximidamidehydrochloride] |
| 20 | N1-pyrrolidine-N5-(4-trifluoromethoxy)phenyl biguanide hydrochloride [N-(N-(4-(trifluoromethoxy)phenyl)carbamimidoyl)pyrrolidine-1-carboximidamidehydrochloride] |
| 21 | N1-piperidine-N5-(4-trifluoromethoxy)phenyl biguanide hydrochloride [N-(N-(4-(trifluoromethoxy)phenyl)carbamimidoyl)piperidine-1-carboximidamidehydrochloride] |
| 22 | N1-piperidine-N5-(4-fluoro-3-trifluoromethyl)phenyl biguanide hydrochloride [N-(N-(4-fluoro-3-(trifluoromethyl)phenyl)carbamimidoyl)piperidine-1-carboximidamidehydrochloride] |
| 23 | N1-piperidine-N5-(4-chloro-3-trifluoromethyl)phenyl biguanide hydrochloride [N-(N-(4-chloro-3-(trifluoromethyl)phenyl)carbamimidoyl)piperidine-1-carboximidamidehydrochloride] |
| 24 | N1-pyrrolidine-N5-(3-fluoro-4-trifluoromethyl)phenyl biguanide hydrochloride [N-(N-(3-fluoro-4-(trifluoromethyl)phenyl)carbamimidoyl)pyrrolidine-1-carboximidamidehydrochloride] |
| 25 | N1-piperidine-N5-(3-fluoro-4-trifluoromethyl)phenyl biguanide hydrochloride [N-(N-(3-fluoro-4-fluoromethyl)phenyl)carbamimidoyl)piperidine-1-carboximidamidehydrochloride] |
| 26 | N1-piperidine-N5-(4-chloro-3-trifluoromethoxy)phenyl biguanide hydrochloride [N-(N-(4-chloro-3-(trifluoromethoxy)phenyl)carbamimidoyl)piperidine-1-carboximidamidehydrochloride] |
| 27 | N1-azetidine-N5-(3-fluoro-4-trifluoromethoxy)phenyl biguanide hydrochloride [N-(N-(3-fluoro-4-(trifluoromethoxy)phenyl)carbamimidoyl)azetidine-1-carboximidamidehydrochloride] |
| 28 | N1-pyrrolidine-N5-(3-fluoro-4-trifluoromethoxy)phenyl biguanide hydrochloride [N-(N-(3-fluoro-4-(trifluoromethoxy)phenyl)carbamimidoyl)pyrrolidine-1-carboximidamidehydrochloride] |
| 29 | N1-piperidine-N5-(3-fluoro-4-trifluoromeihoxy)phenyl biguanide hydrochloride [N-(N-(3-fluoro-4-(trifluoromethoxy)phenyl)carbamimidoyl)piperidine-1-carboximidamidehydrochloride] |
| 30 | N1-azetidine-N5-(3-chloro-4-trifluoromethoxy)phenyl biguanide hydrochloride [N-(N-(3-chloro-4-(trifluoromethoxy)phenyl)carbamimidoyl)azetidine-1-carboximidamidehydrochloride] |
| 31 | N1-pyrrolidine-N5-(3-chloro-4-trifluoromethoxy)phenyl biguanide hydrochloride [N-(N-(3-chloro-4-(trifluoromethoxy)phenyl)carbamimidoyl)pyrrolidine-1-carboximidamidehydrochloride] |
| 32 | N1-piperidine-N5-(3-chloro-4-trifluoromethoxy)phenyl biguanide hydrochloride [N-(N-(3-chloro-4-(trifluoromethoxy)phenyl)carbamimidoyl)piperidine-1-carboximidamidehydrochloride] |
| 33 | N1-piperidine-N5-(3,4-difluoro)phenyl biguanide hydrochloride [N-(N-(3,4-difluorophenyl)carbamimidoyl)piperidine-1-carboximidamidehydrochloride] |

TABLE 1-continued

| Example | Compound |
|---|---|
| 34 | N1-piperidine-N5-(3,5-difluoro)phenyl biguanide hydrochloride [N-(N-(3,5-difluorophenyl)carbamimidoyl)piperidine-1-carboximidamidehydrochloride] |
| 35 | N1-piperidine-N5-(3,5-dichloro)phenyl biguanide hydrochloride [N-(N-(3,5-dichlorophenyl)carbamimidoyl)piperidine-1-carboximidamidehydrochloride] |
| 36 | N1-pyrrolidine-N5-(3,4-dichloro)phenyl biguanide hydrochloride [N-(N-(3,4-dichlorophenyl)carbamimidoyl)pyrrolidine-1-carboximidamidehydrochloride] |
| 37 | N1-piperidine-N5-(3,4-dichloro)phenyl biguanide hydrochloride [N-(N-(3,4-dichlorophenyl)carbamimidoyl)piperidine-1-carboximidamidehydrochloride] |
| 38 | N1-piperidine-N5-(3-chloro-5-trifluoromethoxy)phenyl biguanide hydrochloride [N-(N-(3-chloro-5-(trifluoromethoxy)phenyl)carbamimidoyl)piperidine-1-carboximidamidehydrochloride] |
| 39 | N1-pyrrolidme-N5-(3-bromo-5-trifluoromethoxy)phenyl biguanide hydrochloride [N-(N-(3-bromo-5-(trifluoromethoxy)phenyl)carbamimidoyl)pyrrolidine-1-carboximidamidehydrochloride] |
| 40 | N1-piperidine-N5-(3-bromo-5-trifluoromethoxy)phenyl biguanide hydrochloride [N-(N-(3-bromo-5-(trifluoromethoxy)phenyl)carbamimidoyl)piperidine-1-carboximidamidehydrochloride] |
| 41 | N1-piperidine-N5-(3,4,5-trifluoro)phenyl biguanide hydrochloride [N-(N-(3,4,5-trifluorophenyl)carbamimidoyl)piperidine-1-carboximidamidehydrochloride] |
| 42 | N1-pyrrolidine-N5-(4-trifluoromethyl)phenyl biguanide acetate [N-(N-(4-(trifluoromethyl)phenyl)carbamimidoyl)pyrrolidine-1-carboximidamideacetate] |
| 43 | N1-piperidine-N5-(4-trifluoromethyl)phenyl biguanide acetate [N-(N-(4-(trifluoromethyl)phenyl)carbamimidoyl)piperidine-1-carboximidamideacetate] |
| 44 | N1-pyrrolidine-N5-(4-trifluoromethoxy)phenyl biguanide acetate [N-(N-(4-(trifluoromethoxy)phenyl)carbamimidoyl)pyrrolidine-1-carboximidamideacetate] |
| 45 | N1-piperidine-N5-(4-trifluoromethoxy)phenyl biguanide acetate [N-(N-(4-(trifluoromethoxy)phenyl)carbamimidoyl)piperidine-1-carboximidamideacetate] |
| 46 | N1-pyrrolidine-N5-(3-fluoro-4-trifluoromethyl)phenyl biguanide acetate [N-(N-(3-fluoro-4-(trifluoromethyl)phenyl)carbamimidoyl)pyrrolidine-1-carboximidamideacetate] |
| 47 | N1-piperidine-N5-(3-fluoro-4-trifluoromethyl)phenyl biguanide acetate [N-(N-(3-fluoro-4-(trifluoromethyl)phenyl)carbamimidoyl)piperidine-1-carboximidamideacetate] |
| 48 | N1-pyrrolidine-N5-(3-fluoro-4-trifluoromethoxy)phenyl biguanide acetate [N-N-(3-fluoro-4-fluoromethoxy)phenyl)carbamimidoyl)pyrrolidine-1-carboximidamideacetate] |
| 49 | N1-piperidine-N5-(3-fluoro-4-trifluoromethoxy)phenyl biguanide acetate [N-(N-(3-fluoro-4-(trifluoromethoxy)phenyl)carbamimidoyl)piperidine-1-carboximidamideacetate] |
| 50 | N1-piperidme-N5-(3-trifluoromethyl)benzyl biguanide hydrochloride [N-(N-(3-(trifluoromethyl)benzyl)carbamimidoyl)piperidine-1-carboximidamidehydrochloride] |
| 51 | N1-piperidine-N5-methyl biguanide hydrochloride [N-(N-methylcarbamimidoyl)piperidine-1-carboximidamidehydrochloride] |
| 52 | N1-piperidine-N5-cyclohexyl biguanide hydrochloride [N-(N-cyclohexylcarbamimidoyl)piperidine-1-carboximidamidehydrochloride] |
| 53 | N1-pyrrolidine-N5-cycloheptyl biguanide hydrochloride [N-(N-cycloheptylcarbamimidoyl)pyrrolidine-1-carboximidamidehydrochloride] |
| 54 | N1-piperidine-N5-cycloheptyl biguanide hydrochloride [N-(N-cycloheptylcarbamimidoyl)piperidine-1-carboximidamidehydrochloride] |
| 55 | N1-azepane-N5-cycloheptyl biguanide hydrochloride [N-(N-cycloheptylcarbamimidoyl)azepane-1-carboximidamidehydrochloride] |
| 56 | N1-piperidine-N5-(4-methyl)benzyl biguanide hydrochloride [N-(N-(4-methylbenzyl)carbamimidoyl)piperidine-1-carboximidamidehydrochloride] |
| 57 | N1-piperidine-N5-(4-methoxy)benzyl biguanide hydrochloride [N-(N-(4-methoxybenzyl)carbamimidoyl)piperidine-1-carboximidamidehydrochloride] |
| 58 | N1-pyrrolidine-N5-(4-chloro)benzyl biguanide hydrochloride [N-(N-(4-chlorobenzyl)carbamimidoyl)pyrrolidine-1-carboximidamidehydrochloride] |
| 59 | N1-azepane-N5-(4-chloro)benzyl biguanide hydrochloride [N-(N-(4-chlorobenzyl)carbamimidoyl)azepane-1-carboximidamidehydrochloride] |
| 60 | N1-piperidine-N5-(4-trifluoromethyl)benzyl biguanide hydrochloride [N-(N-(4-(trifluoromethyl)benzyl)carbamimidoyl)piperidine-1-carboximidamidehydrochloride] |

TABLE 1-continued

| Example | Compound |
|---|---|
| 61 | N1-azetidine-N5-(4-trifluoromethoxy)benzyl biguanide hydrochloride [N-(N-(4-(trifluoromethoxy)benzyl)carbamimidoyl)azetidine-1-carboximidamidehydrochloride] |
| 62 | N1-pyrrolidine-N5-(4-trifluoromethoxy)benzyl biguanide hydrochloride [N-(N-(4-(trifluoromethoxy)benzyl)carbamimidoyl)pyrrolidine-1-carboximidamidehydrochloride] |
| 63 | N1-piperidine-N5-(4-trifluoromethoxy)benzyl biguanide hydrochloride [N-(N-(4-(trifluoromethoxy)benzyl)carbamimidoyl)piperidine-1-carboximidamidehydrochloride] |
| 64 | N1-piperidine-N5-(4-fluoro-3-trifluoromethyl)benzyl biguanide hydrochloride [N-(N-(4-fluoro-3-(trifluoromethyl)benzyl)carbamimidoyl)piperidine-1-carboximidamidehydrochloride] |
| 65 | N1-piperidine-N5-(4-chloro-3-trifluoromethyl)benzyl biguanide hydrochloride [N-(N-(4-chloro-3-(trifluoromethyl)benzyl)carbamimidoyl)piperidine-1-carboximidamidehydrochloride] |
| 66 | N1-piperidine-N5-(3-fluoro-4-trifluoromethyl)benzyl biguanide hydrochloride [N-(N-(3-fluoro-4-(trifluoromethyl)benzyl)carbamimidoyl)piperidine-1-carboximidamidehydrochloride] |
| 67 | N1-piperidine-N5-(3-chloro-4-trifluoromethyl)benzyl biguanide hydrochloride [N-(N-(3-chloro-4-(trifluoromethyl)benzyl)carbamimidoyl)piperidine-1-carboximidamidehydrochloride] |
| 68 | N1-piperidine-N5-(4-fluoro-3-trifluoromethoxy)benzyl biguanide hydrochloride [N-(N-(4-fluoro-3-(trifluoromethoxy)benzyl)carbamimidoyl)piperidine-1-carboximidamidehydrochloride] |
| 69 | N1-piperidine-N5-(3-chloro-4-trifluoromethoxy)benzyl biguanide hydrochloride [N-(N-(3-chloro-4-(trifluoromethoxy)benzyl)carbamimidoyl)piperidme-1-carboximidamidehydrochloride] |
| 70 | N1-piperidine-N5-(2,6-difluoro)benzyl biguanide hydrochloride [N-(N-(2,6-difluorobenzyl)carbamimidoyl)piperidine-1-carboximidamidehydrochloride] |
| 71 | N1-piperidine-N5-(3.4-difluoro)benzyl biguanide hydrochloride [N-(N-(3,4-difluorobenzyl)carbamimidoyl)piperidine-1-carboximidamidehydrochloride] |
| 72 | N1-piperidine-N5-(2,4-dichloro)benzyl biguanide hydrochloride [N-(N-(2,4-dichlorobenzyl)carbamimidoyl)piperidine-1-carboximidamidehydrochloride] |
| 73 | N1-pyrrolidine-N5-(3,4-dichloro)benzyl biguanide hydrochloride [N-(N-(3,4-dichlorobenzyl)carbamimidoyl)pyrrolidine-1-carboximidamidehydrochloride] |
| 74 | N1-piperidine-N5-(3,4-dichloro)benzyl biguanide hydrochloride [N-(N-(3,4-dichlorobenzyl)carbamimidoyl)piperidine-1-carboximidamidehydrochloride] |
| 75 | N1-piperidine-N5-(thiophen-2-yl)ethyl biguanide hydrochloride [N-(N-(2-(thiophen-2-yl)ethyl)carbamimidoyl)piperidine-1-carboximidamidehydrochloride] |
| 76 | N1-pyrrolidine-N5-(phenethyl) biguanide hydrochloride [N-(N-phenethylcarbamimidoyl)pyrrolidine-1-carboximidamidehydrochloride] |
| 77 | N1-piperidine-N5-(phenethyl) biguanide hydrochloride [N-(N-phenethylcarbamimidoyl)piperidine-1-carboximidamidehydrochloride] |
| 78 | N1-azepane-N5-(phenethyl) biguanide hydrochloride [N-(N-phenethylcarbamimidoyl)azepane-1-carboximidamidehydrochloride] |
| 79 | N1-azepane-N5-((4-fluoro)phenethyl) biguanide hydrochloride [N-(N-(4-fluorophenethyl)carbamimidoyl)azepane-1-carboximidamidehydrochloride] |
| 80 | N1-azepane-N5-((4-chloro)phenethyl) biguanide hydrochloride [N-(N-(4-chlorophenethyl)carbamimidoyl)azepane-1-carboximidamidehydrochloride] |
| 81 | N1-pyrrole-N5-(4-trifluoromethoxy)phenyl biguanide hydrochloride [N-(N-(4-(trifluoromethoxy)phenyl)carbamimidoyl)-2,5-dihydro-1H-pyrrole-1-carboximidamide hydrochloride] |
| 82 | N1-pyrrole-N5-(4-trifluoromethyl)phenyl biguanide hydrochloride [N-(N-(4-(trifluoromethyl)phenyl)carbamimidoyl)-2,5-dihydro-1H-pyrrole-1-carboximidamide hydrochloride] |
| 83 | N1-pyrrole-N5-(3-trifluoromethyl)phenyl biguanide hydrochloride [N-(N-(3-(trifluoromethyl)phenyl)carbamimidoyl)-2,5-dihydro-1H-pyrrole-1-carboximidamide hydrochloride] |
| 84 | N1-pyrrole-N5-(4-fluoro)phenyl biguanide hydrochloride [N-(N-(4-fluorophenyl)carbamimidoyl)-2,5-dihydro-1H-pyrrole-1-carboximidamide hydrochloride] |
| 85 | N1-pyrrole-N5-(4-chloro)phenyl biguanide hydrochloride [N-(N-(4-chlorophenyl)carbamimidoyl)-2,5-dihydro-1H-pyrrole-1-carboximidamide hydrochloride] |
| 86 | N1-pyrrole-N5-(4-bromo)phenyl biguanide hydrochloride [N-(N-(4-bromophenyl)carbamimidoyl)-2,5-dihydro-1H-pyrrole-1-carboximidamide hydrochloride] |
| 87 | N1-pyrrole-N5-(3-chloro,4-trifluoromethoxy)phenyl biguanide hydrochloride [N-(N-(3-chloro-4-(trifluoromethoxy)phenyl)carbamimidoyl)-2,5-dihydro-1H-pyrrole-1-carboximidamide hydrochloride] |

TABLE 1-continued

| Example | Compound |
|---|---|
| 88 | N1-dihydropyridme-N5-(3-chloro,4-trifluoromethoxy)phenyl biguanide hydrochloride<br>[N-(N-(3-chloro-4-(trifluoromethoxy)phenyl)carbamimidoyl)-5,6-dihydropyridine-1(2H)-carboximidamide hydrochloride] |
| 89 | N1-pyrrole-N5-(3-trifluoromethyl)benzyl biguanide hydrochloride<br>[N-(N-(3-(trifluoromethyl)benzyl)carbamimidoyl)-2,5-dihydro-1H-pyrrole-1-carboximidamide hydrochloride] |
| 90 | N1-pyrrole-N5-(4-trifluoromethyl)benzyl biguanide hydrochloride<br>[N-(N-(4-(trifluoromethyl)benzyl)carbamimidoyl)-2,5-dihydro-1H-pyrrole-1-carboximidamide hydrochloride] |
| 91 | N1-pyrrole-N5-(3-trifluoromethoxy)benzyl biguanide hydrochloride<br>[N-(N-(3-(trifluoromethoxy)benzyl)carbamimidoyl)-2,5-dihydro-1H-pyrrole-1-carboximidamide hydrochloride] |
| 92 | N1-(3-methyl)pyrrole-N5-(4-trifluoromethoxy)phenyl biguanide hydrochloride<br>[3-methyl-N-(N-(4-(trifluoromethoxy)phenyl)carbamimidoyl)-2,5-dihydro-1H-pyrrole-1-carboximidamide hydrochloride] |
| 93 | N1-(3-methyl)pyrrole-N5-(4-trifluoromethyl)phenyl biguanide hydrochloride<br>[3-methyl-N-(N-(4-(trifluoromethyl)phenyl)carbamimidoyl)-2,5-dihydro-1H-pyrrole-1-carboximidamide hydrochloride] |
| 94 | N1-(3-methyl)pyrrole-N5-(4-chloro)phenyl biguanide hydrochloride<br>[N-(N-(4-chlorophenyl)carbamimidoyl)-3-methyl-2,5-dihydro-1H-pyrrole-1-carboximidamide hydrochloride] |
| 95 | N1-(3-methyl)pyrrole-N5-(4-chloro,3-trifluoromethyl)phenyl biguanide hydrochloride<br>[N-(N-(4-chloro-3-(trifluoromethyl)phenyl)carbamimidoyl)-3-methyl-2,5-dihydro-1H-pyrrole-1-carboximidamide hydrochloride] |
| 96 | N1-(3-methyl)pyrrole-N5-(3-trifluoroinethyl)phenyl biguanide hydrochloride<br>[3-methyl-N-(N-(3-(trifluoromethyl)phenyl)carbamimidoyl)-2,5-dihydro-1H-pyrrole-1-carboximidamide hydrochloride] |
| 97 | N1-(3-methyl)pyrrole-N5-(4-fluoro)phenyl biguanide hydrochloride<br>[N-(N-(4-fluorophenyl)carbamimidoyl)-3-methyl-2,5-dihydro-1H-pyrrole-1-carboximidamide hydrochloride] |
| 98 | N1-(3-methyl)pyrrole-N5-(4-bromo)phenyl biguanide hydrochloride<br>[N-(N-(4-bromophenyl)carbamimidoyl)-3-methyl-2,5-dihydro-1H-pyrrole-1-carboximidamide hydrochloride] |
| 99 | N1-(3-methyl)pyrrole-N5-(4-methoxy)phenyl biguanide hydrochloride<br>[N-(N-(4-methoxyphenyl)carbamimidoyl)-3-methyl-2,5-dihydro-1H-pyrrole-1-carboximidamide hydrochloride] |
| 100 | N1-(3-methyl)pyrrole-N5-(3,4-dimethoxy)phenyl biguanide hydrochloride<br>[N-(N-(3,4-dimethoxyphenyl)carbamimidoyl)-3-methyl-2,5-dihydro-1H-pyrrole-1-carboximidamide hydrochloride] |
| 101 | N1-(3-methyl)pyrrole-N5-(4-methoxy)benzyl biguanide hydrochloride<br>[3-methyl-N-(N-(4-(trifluoromethoxy)benzyl)carbamimidoyl)-2,5-dihydro-1H-pyrrole-1-carboximidamide hydrochloride] |
| 102 | N1-(3-methyl)pyrrole-N5-(3-methoxy)phenyl biguanide hydrochloride<br>[3-methyl-N-(N-(3-(trifluoromethoxy)phenyl)carbamimidoyl)-2,5-dihydro-1H-pyrrole-1-carboximidamide hydrochloride] |
| 103 | N1-(3-methyl)pyrrole-N5-(4-trifluoromethyl)benzyl biguanide hydrochloride<br>[3-methyl-N-(N-(4-(trifluoromethyl)benzyl)carbamimidoyl)-2,5-dihydro-1H-pyrrole-1-carboximidamide hydrochloride] |
| 104 | N1-(3-methyl)pyrrole-N5-(4-chloro,3-trifluoromethyl)benzyl biguanide hydrochloride<br>[N-(N-(4-chloro-3-(trifluoromethyl)benzyl)carbamimidoyl)-3-methyl-2,5-dihydro-1H-pyrrole-1-carboximidamide hydrochloride] |
| 105 | N1-dihydropyridine-N5-(4-trifluoromethoxy)phenyl biguanide hydrochloride<br>[N-(N-(4-(trifluoromethoxy)phenyl)carbamimidoyl)-5,6-dihydropyridine-1(2H)-carboximidamide hydrochloride] |
| 106 | N1-dihydropyridine-N5-(4-trifluoromethyl)phenyl biguanide hydrochloride<br>[N-(N-(4-(trifluoromethyl)phenyl)carbamimidoyl)-5,6-dihydropyridine-1(2H)-carboximidamide hydrochloride] |
| 107 | N1-dihydropyridine-N5-(3-trifluoromethoxy)phenyl biguanide hydrochloride<br>[N-(N-(3-(trifluoromethoxy)phenyl)carbamimidoyl)-5,6-dihydropyridine-1(2H)-carboximidamide hydrochloride] |
| 108 | N1-dihydropyridine-N5-(3-trifluoromethyl)phenyl biguanide hydrochloride<br>[N-(N-(3-(trifluoromethyl)phenyl)carbamimidoyl)-5,6-dihydropyridine-1(2H)-carboximidamide hydrochloride] |
| 109 | N1-dihydropyridine-N5-(4-fluoro,3-trifluoromethyl)phenyl biguanide hydrochloride<br>[N-(N-(4-fluoro-3-(trifluoromethyl)phenyl)carbamimidoyl)-5,6-dihydropyridine-1(2H)-carboximidamide hydrochloride] |
| 110 | N1-dihydropyridine-N5-(3-chloro,4-trifluoromethoxy)phenyl biguanide hydrochloride<br>[N-(N-(4-chloro-3-(trifluoromethyl)phenyl)carbamimidoyl)-5,6-dihydropyridine-1(2H)-carboximidamide hydrochloride] |
| 111 | N1-dihydropyridine-N5-(3-fluoro,4-trifluoromethoxy)phenyl biguanide hydrochloride<br>[N-(N-(3-fluoro-4-(trifluoromethoxy)phenyl)carbamimidoyl)-5,6-dihydropyridine-1(2H)-carboximidamide hydrochloride] |

TABLE 1-continued

| Example | Compound |
|---|---|
| 112 | N1-dihydropyridine-N5-(4-chloro)phenyl biguanide hydrochloride [N-(N-(4-chlorophenyl)carbamimidoyl)-5,6-dihydropyridine-1(2H)-carboximidamide hydrochloride] |
| 113 | N1-dihydropyridine-N5-(4-bromo)phenyl biguanide hydrochloride [N-(N-(4-bromophenyl)carbamimidoyl)-5,6-dihydropyridine-1(2H)-carboximidamide hydrochloride] |
| 114 | N1-dihydropyridine-N5-(4-fluoro)phenyl biguanide hydrochloride [N-(N-(4-fluorophenyl)carbamimidoyl)-5,6-dihydropyridine-1(2H)-carboximidamide hydrochloride] |
| 115 | N1-dihydropyridine-N5-(3,5-dimethoxy)phenyl biguanide hydrochloride [N-(N-(3,5-dimethoxyphenyl)carbamimidoyl)-5,6-dihydropyridine-1(2H)-carboximidamide hydrochloride] |
| 116 | N1-dihydropyridine-N5-phenyl biguanide hydrochloride [N-(N-phenylcarbamimidoyl)-5,6-dihydropyridine-1(2H)-carboximidamide hydrochloride] |
| 117 | N1-dihydropyridine-N5-(4-methoxy)phenyl biguanide hydrochloride [N-(N-(4-methoxyphenyl)carbamimidoyl)-5,6-dihydropyridine-1(2H)-carboximidamide hydrochloride] |
| 118 | N1-dihydropyridine-N5-(3-methoxy)phenyl biguanide hydrochloride [N-(N-(3-methoxyphenyl)carbamimidoyl)-5,6-dihydropyridine-1(2H)-carboximidamide hydrochloride] |
| 119 | N1-pyrrole-N5-(3-trifluoromethyl)phenyl biguanide hydrochloride [N-(N-(4-methoxyphenyl)carbamimidoyl)-2,5-dihydro-1H-pyrrole-1-carboximidamide hydrochloride] |
| 120 | N1-pyrrole-N5-(3-trifluoromethoxy)phenyl biguanide hydrochloride [N-(N-(3-methoxyphenyl)carbamimidoyl)-2,5-dihydro-1H-pyrrole-1-carboximidamide hydrochloride] |
| 121 | N1-pyrrole-N5-phenyl biguanide hydrochloride [N-(N-phenylcarbamimidoyl)-2,5-dihydro-1H-pyrrole-1-carboximidamide hydrochloride] |
| 122 | N1-pyrrole-N5-(3,5-dimethoxy)phenyl biguanide hydrochloride [N-(N-(3,5-dimethoxyphenyl)carbamimidoyl)-2,5-dihydro-1H-pyrrole-1-carboximidamide hydrochloride] |
| 123 | N1-pyrrole-N5-(4-fluoro,3-trifluoromethyl)phenyl biguanide hydrochloride [N-(N-(4-fluoro-3-(trifluoromethyl)phenyl)carbamimidoyl)-2,5-dihydro-1H-pyrrole-1-carboximidamide hydrochloride] |
| 124 | N1-pyrrole-N5-(3-fluoro,4-trifluoromethyl)phenyl biguanide hydrochloride [N-(N-(3-fluoro-4-(trifluoromethyl)phenyl)carbamimidoyl)-2,5-dihydro-1H-pyrrole-1-carboximidamide hydrochloride] |
| 125 | N1-dihydropyridine-N5-(4-methyl)phenyl biguanide hydrochloride [N-(N-p-tolylcarbamimidoyl)-5,6-dihydropyridine-1(2H)-carboximidamide hydrochloride] |
| 126 | N1-dihydropyridine-N5-(3-methyl)phenyl biguanide hydrochloride [N-(N-m-tolylcarbamimidoyl)-5,6-dihydropyridine-1(2H)-carboximidamide hydrochloride] |
| 127 | N1-pyrrole-N5-(4-methyl)phenyl biguanide hydrochloride [N-(N-p-tolylcarbamimidoyl)-2,5-dihydro-1H-pyrrole-1-carboximidamide hydrochloride] |
| 128 | N1-pyrrole-N5-(3-methyl)phenyl biguanide hydrochloride [N-(N-m-tolylcarbamimidoyl)-2,5-dihydro-1H-pyrrole-1-carboximidamide hydrochloride] |
| 129 | N1-pyrrole-N5-(3-trifluoromethoxy)phenyl biguanide hydrochloride [N-(N-(3-(trifluoromethoxy)phenyl)carbamimidoyl)-2,5-dihydro-1H-pyrrole-1-carboximidamide hydrochloride] |
| 130 | N1-dihydropyridine-N5-hexyl biguanide hydrochloride [N-(N-hexylcarbamimidoyl)-5,6-dihydropyridine-1(2H)-carboximidamide hydrochloride] |
| 131 | N1-dihydropyridine-N5-(4-trifluoromethoxy)benzyl biguanide hydrochloride [N-(N-(4-(trifluoromethoxy)benzyl)carbamimidoyl)-5,6-dihydropyridine-1(2H)-carboximidamide hydrochloride] |
| 132 | N1-dihydropyridine-N5-(3-trifluoromethoxy)benzyl biguanide hydrochloride [N-(N-(3-(trifluoromethoxy)benzyl)carbamimidoyl)-5,6-dihydropyridine-1(2H)-carboximidamide hydrochloride] |
| 133 | N1-dihydropyridine-N5-(4-trifluoromethyl)benzyl biguanide hydrochloride [N-(N-(4-(trifluoromethyl)benzyl)carbamimidoyl)-5,6-dihydropyridine-1(2H)-carboximidamide hydrochloride] |
| 134 | N1-dihydropyridine-N5-(3-trifluoromethyl)benzyl biguanide hydrochloride [N-(N-(3-(trifluoromethyl)benzyl)carbamimidoyl)-5,6-dihydropyridine-1(2H)-carboximidamide hydrochloride] |
| 135 | N1-dihydropyridine-N5-(4-chloro,3-trifluoromethyl)benzyl biguanide hydrochloride [N-(N-(4-chloro-3-(trifluoromethyl)benzyl)carbamimidoyl)-5,6-dihydropyridine-1(2H)-carboximidamide hydrochloride] |
| 136 | N1-dihydropyridine-N5-butyl biguanide hydrochloride [N-(N-butylcarbamimidoyl)-5,6-dihydropyridine-1(2H)-carboximidamide hydrochloride] |

TABLE 1-continued

| Example | Compound |
|---|---|
| 137 | N1-dihydropyridine-N5-propyl biguanide hydrochloride [N-(N-propylcarbamimidoyl)-5,6-dihydropyridine-1(2H)-carboximidamide hydrochloride] |
| 138 | N1-dihydropyridine biguanide hydrochloride [N-carbamimidoyl-5,6-dihydropyridine-1(2H)-carboximidamide hydrochloride] |
| 139 | N1-(3-methyl)piperidine-N5-(3-trifluoromethyl)benzyl biguanide hydrochloride [3-methyl-N-(N-(3-(trifluoromethyl)benzyl)carbamimidoyl)piperidine-1-carboximidamide hydrochloride] |
| 140 | N1-(3-methyl)piperidine-N5-(4-chloro)benzyl biguanide hydrochloride [N-(N-(4-chlorobenzyl)carbamimidoyl)-3-methylpiperidine-1-carboximidamide hydrochloride] |
| 141 | N1-(3-methyl)piperidine-N5-(4-fluoro)phenyl biguanide hydrochloride [N-(N-(4-fluorophenyl)carbamimidoyl)-3-methylpiperidine-1-carboximidamide hydrochloride] |
| 142 | N1-(3-methyl)piperidine-N5-(4-bromo)phenyl biguanide hydrochloride [N-(N-(4-bromophenyl)carbamimidoyl)-3-methylpiperidine-1-carboximidamide hydrochloride] |
| 143 | N1-(3-methyl)piperidine-N5-(4-chloro,3-trifluoromethyl)phenyl biguanide hydrochloride [N-(N-(4-chloro-3-(trifluoromethyl)phenyl)carbamimidoyl)-3-methylpiperidine-1-carboximidamide hydrochloride] |
| 144 | N1-(3-methyl)piperidine-N5-(3-fluoro,4-trifluoromethyl)phenyl biguanide hydrochloride [N-(N-(3-fluoro-4-(trifluoromethyl)phenyl)carbamimidoyl)-3-methylpiperidine-1-carboximidamide hydrochloride] |
| 145 | N1-(3-methyl)piperidine-N5-(4-fluoro,3-trifluoromethyl)phenyl biguanide hydrochloride [N-(N-(4-fluoro-3-(trifluoromethyl)phenyl)carbamimidoyl)-3-methylpiperidine-1-carboximidamide hydrochloride] |
| 146 | N1-(2-methyl)piperidine-N5-(4-trifluoromethoxy)phenyl biguanide hydrochloride [2-methyl-N-(N-(4-(trifluoromethoxy)phenyl)carbamimidoyl)piperidine-1-carboximidamide hydrochloride] |
| 147 | N1-(2-methyl)piperidine-N5-(3-trifluoromethoxy)phenyl biguanide hydrochloride [2-methyl-N-(N-(3-(trifluoromethoxy)phenyl)carbamimidoyl)piperidine-1-carboximidamide hydrochloride] |
| 148 | N1-(2-methyl)piperidine-N5-(4-trifluoromethyl)phenyl biguanide hydrochloride [2-methyl-N-(N-(4-(trifluoromethyl)phenyl)carbamimidoyl)piperidine-1-carboximidamide hydrochloride] |
| 149 | N1-(3-methyl)piperidine-N5-(3-fluoro,4-trifluoromethoxy)phenyl biguanide hydrochloride [N-(N-(3-fluoro-4-(trifluoromethoxy)phenyl)carbamimidoyl)-3-methylpiperidine-1-carboximidamide hydrochloride] |
| 150 | N1-(2-methyl)piperidine-N5-(3-fluoro,4-trifluoromethoxy)phenyl biguanide hydrochloride [N-(N-(3-fluoro-4-(trifluoromethoxy)phenyl)carbamimidoyl)-2-methylpiperidine-1-carboximidamide hydrochloride] |
| 151 | N1-(2-methyl)piperidine-N5-(4-chloro)phenyl biguanide hydrochloride [N-(N-(4-chlorophenyl)carbamimidoyl)-2-methylpiperidine-1-carboximidamide hydrochloride] |
| 152 | N1-(2-methyl)piperidine-N5-(4-fluoro,3-trifluoromethyl)phenyl biguanide hydrochloride [N-(N-(4-fluoro-3-(trifluoromethyl)phenyl)carbamimidoyl)-2-methylpiperidine-1-carboximidamide hydrochloride] |
| 153 | N1-(2-methyl)piperidine-N5-(3-trifluoromethyl)phenyl biguanide hydrochloride [2-methyl-N-(N-(3-(trifluoromethyl)phenyl)carbamimidoyl)piperidine-1-carboximidamide hydrochloride] |
| 154 | N1-(2-methyl)piperidine-N5-(4-chloro,3-trifluoromethyl)phenyl biguanide hydrochloride [N-(N-(4-chloro-3-(trifluoromethyl)phenyl)carbamimidoyl)-2-methylpiperidine-1-carboximidamide hydrochloride] |
| 155 | N1-(3-methyl)piperidine-N5-(4-trifluoromethyl)phenyl biguanide hydrochloride [3-methyl-N-(N-(4-(trifluoromethyl)phenyl)carbamimidoyl)piperidine-1-carboximidamide hydrochloride] |
| 156 | N1-(3-methyl)piperidine-N5-(4-trifluoromethoxy)phenyl biguanide hydrochloride [3-methyl-N-(N-(4-(trifluoromethoxy)phenyl)carbamimidoyl)piperidine-1-carboximidamide hydrochloride] |
| 157 | N1-(3-methyl)piperidine-N5-(3-trifluoromethoxy)phenyl biguanide hydrochloride [3-methyl-N-(N-(3-(trifluoromethoxy)phenyl)carbamimidoyl)piperidine-1-carboximidamide hydrochloride] |
| 158 | N1-(3-methyl)piperidine-N5-(4-trifluoromethoxy)benzyl biguanide hydrochloride [3-methyl-N-(N-(4-(trifluoromethoxy)benzyl)carbamimidoyl)piperidine-1-carboximidamide hydrochloride] |

TABLE 1-continued

| Example | Compound |
|---------|----------|
| 159 | N1-(3-methyl)piperidine-N5-(4-fluoro,3-trifluoromethyl)phenyl biguanide hydrochloride<br>[N-(N-(4-fluoro-3-(trifluoromethyl)phenyl)carbamimidoyl)-3-methylpiperidine-1-carboximidamide hydrochloride] |
| 160 | N1-(3-methyl)piperidine-N5-(4-trifluoromethyl)benzyl biguanide hydrochloride<br>[3-methyl-N-(N-(4-(trifluoromethyl)benzyl)carbamimidoyl)piperidine-1-carboximidamide hydrochloride] |
| 161 | N1-(3-methyl)piperidine-N5-(4-chloro)phenyl biguanide hydrochloride<br>[3-methyl-N-(N-(3-(trifluoromethyl)benzyl)carbamimidoyl)piperidine-1-carboximidamide hydrochloride] |
| 162 | N1-(3-methyl)piperidine-N5-(3-trifluoromethyl)phenyl biguanide hydrochloride<br>[3-methyl-N-(N-(3-(trifluoromethyl)phenyl)carbamimidoyl)piperidine-1-carboximidamide hydrochloride] |
| 163 | N1-(3-methyl)piperidine-N5-(4-fluoro,3-trifluoromethyl)phenyl biguanide hydrochloride<br>[2,6-dimethyl-N-(N-(4-(trifluoromethoxy)phenyl)carbamimidoyl)piperidine-1-carboximidamide hydrochloride] |
| 164 | N1-(3-methyl)piperidine-N5-(4-fluoro,3-trifluoromethyl)phenyl biguanide hydrochloride<br>[2,6-dimethyl-N-(N-(3-(trifluoromethoxy)phenyl)carbamimidoyl)piperidine-1-carboximidamide hydrochloride |
| 165 | N1-(3-methyl)piperidine-N5-(4-fluoro,3-trifluoromethyl)phenyl biguanide hydrochloride<br>[2,6-dimethyl-N-(N-(4-(trifluoromethyl)phenyl)carbamimidoyl)piperidine-1-carboximidamide hydrochloride] |
| 166 | N1-(2,6-dimethyl)piperidine-N5-(3-trifluoromethyl)phenyl biguanide hydrochloride<br>[2,6-dimethyl-N-(N-(3-(trifluoromethyl)phenyl)carbamimidoyl)piperidine-1-carboximidamide hydrochloride] |
| 167 | N1-(2,6-dimethyl)piperidine-N5-(4-fluoro,3-trifluoromethyl)phenyl biguanide hydrochloride<br>[N-(N-(4-fluoro-3-(trifluoromethyl)phenyl)carbamimidoyl)-2,6-dimethylpiperidine-1-carboximidamide hydrochloride] |
| 168 | N1-(2,6-dimethyl)piperidine-N5-(4-chloro,3-trifluoromethyl)phenyl biguanide hydrochloride<br>[N-(N-(4-chloro-3-(trifluoromethyl)phenyl)carbamimidoyl)-2,6-dimethylpiperidine-1-carboximidamide hydrochloride] |
| 169 | N1-(2,6-dimethyl)piperidine-N5-(3-fluoro,4-trifluoromethoxy)phenyl biguanide hydrochloride<br>[N-(N-(3-fluoro-4-(trifluoromethoxy)phenyl)carbamimidoyl)-2,6-dimethylpiperidine-1-carboximidamide hydrochloride] |
| 170 | N1-(2,6-dimethyl)piperidine-N5-(4-chloro)phenyl biguanide hydrochloride<br>[N-(N-(4-chlorophenyl)carbamimidoyl)-2,6-dimethylpiperidine-1-carboximidamide hydrochloride] |
| 171 | N1-(2,6-dimethyl)piperidine-N5-(4-bromo)phenyl biguanide hydrochloride<br>[N-(N-(4-bromophenyl)carbamimidoyl)-2,6-dimethylpiperidine-1-carboximidamide hydrochloride] |
| 172 | N1-(2,6-dimethyl)piperidine-N5-(4-fluoro)phenyl biguanide hydrochloride<br>[N-(N-(4-fluorophenyl)carbamimidoyl)-2,6-dimethylpiperidine-1-carboximidamide hydrochloride] |

Experimental Example 1: Observation of EMT-Suppressing Effect of Biguanide Derivatives of Formula 1

In order to examine the EMT-suppressing effect of biguanide derivatives of Formula 1 according to the present invention, they were evaluated using Snail, an EMT-related transcription factor. After treating MCF7 cells derived from human breast cancer with the compounds of Examples, the changes in Snail were examined and compared with those of control materials, i.e., metformin and phenformin, which are known to have an EMT-suppressing effect.

As a result, it was confirmed that metformin failed to suppress the expression of Snail at a concentration of 1000 μM, while phenformin did not show any effect regarding the suppression of Snail expression even at a concentration of 10 μM, as shown in FIG. 1. In contrast, the biguanide derivative of Formula 1 (the compound of Example 44) according to the present invention was shown to strongly suppress the expression of Snail even at a concentration of 5 μM, thus confirming the EMT-suppressing effect.

Experimental Example 2: Confirmation of Therapeutic Effect in Model with Peritoneal Fibrosis Peritoneal fibrosis is a disease that can cause obstruction of ureters, aorta, and inferior vena cava due to invasion of inflammatory cells and proliferation of fibrous tissues in the peritoneum, and also can cause hardening of various organs such as pancreas, bile duct, liver, lung, and salivary gland. As is the case with other fibroses, the EMT induced by TGF-b has been known to be a major cause of the occurrence of peritoneal fibrosis and insufficiency of peritoneal functions.

In order to confirm the effect of the biguanide derivatives according to the present invention on the improvement of peritoneal fibrosis, experiments were performed as shown below.

Six-week old male wistar rats (150 g to 200 g, 60 rats) were divided into the following four groups:
 1) Normal group treated with only a vehicle (Control);
 2) Group having peritoneal fibrosis, induced to have peritoneal fibrosis but not treated with any drug (PF);

3) Group simultaneously treated with a peritoneal fibrosis-causing drug and 1 mg/kg of the compound of Example 44 according to the present invention (CG+substance 1 mg/kg); and 4) Group simultaneously treated with a peritoneal fibrosis-causing drug and 10 mg/kg of the compound of Example 44 according to the present invention (CG+substance 10 mg/kg).

The rats in the three experimental groups, excluding the normal group treated with only a vehicle, were intraperitoneally injected with 2 mL of chlorhexidine gluconate (CG), which is a peritoneal fibrosis-causing drug, for 4 weeks.

Generally, peritoneum is divided into visceral peritoneum, which encompasses the internal viscera such as the liver, stomach, small intestine, large intestine, and parietal peritoneum, which encompasses the peritoneal wall. In this experiment, the thickness of the peritoneal membrane, which corresponds to the parietal peritoneum, and the liver membrane, which corresponds to the visceral peritoneum, and the level of fibrosis were examined.

As a result, as can be confirmed in FIG. 2, it was confirmed that the peritoneal fibrosis was induced by the administration of CG, thereby thickening the peritoneal membrane, and in the cases of experimental groups, the fibrosis was completely recovered and normalized by the biguanide derivative according to the present invention. This phenomenon was also confirmed in the case of the liver membrane by CG treatment.

Additionally, as the result of scaled thickness of the peritoneal membrane and the liver membrane shown in FIG. 2, the thickness of the peritoneal membrane and the liver membrane was significantly increased by CG treatment and also completely normalized by the treatment of the biguanide derivatives, as shown in FIG. 3.

Experimental Example 3: Confirmation of EMT-Related Transcription Factors Using Peritoneal Tissues in Model with Peritoneal Fibrosis When patients with terminal renal failure receive peritoneal dialysis, peritoneal fibrosis starts to proceed due to the continuous inflammation in the peritoneal membrane. This is due to long-term administration of a peritoneal dialysis solution containing high glucose concentration, and the effect of the compound of Example 44 was confirmed by inducing high glucose concentration in the peritoneal mesothelial cells of male wistar rats in this experiment. That is, this experiment was designed to examine the morphological change in the peritoneal mesothelial cells by high glucose treatment along with the expression levels of mRNA and proteins of fibrosis-mediating materials and the ECM-related materials.

To this end, the peritonea of the male wistar rats were dissected and their peritoneal mesothelial cells were subjected to primary culture using 0.25% trypsin-EDTA. The experiment was performed after dividing them into the following three groups:

1) Group treated with Normal glucose (NG, 5 mM);
2) Group treated with High glucose (HG, 30 mM); and
3) Group treated with HG and the compound of Example 44 at various concentrations (10 μM, 20 μM, 30 μM, and 50 μM).

After culturing the cells in each group under the given conditions, the expression levels of mRNAs and proteins of the fibrosis-mediating materials and the ECM-related materials were analyzed by RT-PCR and western blot analysis.

As a result, as shown in FIG. 4, the expression levels of mRNAs and proteins of smad3, which is a marker for fibrosis, and Snail were shown to increase by HG treatment (30 mM). Additionally, it was confirmed that the levels of smad3, mRNA, and protein of Snail, which were increased by HG treatment, were decreased by the treatment of the biguanide derivative of Formula 1 according to the present invention in a dose-dependent manner.

Additionally, when the morphological changes in peritoneal mesothelial cells obtained from the peritonea were examined, the morphology of the cells, which turned into myofibroblasts by high glucose treatment, was returned to maintain a shape similar to that of the normal ones (a cobblestone shape) by the treatment with the biguanide derivative of Formula 1 (the compound of Example 44, 100 μM), as shown in FIG. 5.

As investigated by the above experiments, it was confirmed that the biguanide derivatives of Formula 1 according to the present invention can effectively suppress the EMT actions, and thus they can be used for preventing and treating fibrosis.

Experimental Example 4: Confirmation of Therapeutic Effect in Model with Renal Fibrosis This study was performed by an in vivo experiment using an animal model with unilateral ureteral obstruction and an in vitro experiment focused on proximal tubular cells and distal tubular cells. The in vivo and in vitro experiments were performed in parallel.

A. In Vivo Experiment

An animal model with unilateral ureteral obstruction (UUO) for renal fibrosis was prepared using male wistar rats (6-week old, 150 g to 200 g).

Experimental groups were divided into the following four groups (n=7 per each group):

1) Group with operation only without a ligation of ureters (sham); 2) Group treated with the biguanide derivative of Formula 1 (the compound of Example 44) according to the present invention on the sham Group without a ligation of ureter (sham+drug); 3) Group with a ligation of ureters (UUO); and 4) Group treated with the biguanide derivative of Formula 1 (the compound of Example 44) according to the present invention on the UUO Group (UUO+drug).

The rats in Group 3 and Group 4 were induced to have a lateral ureteral obstruction by subjecting them to inhalation anesthesia, cutting their abdomens open, and tying their left ureters up twice using surgical thread (4-0 silk), followed by ligation. Additionally, Group 2 and Group 4 were treated with the drug for 10 days.

The rats in all groups were euthanized on the $10^{th}$ day of the experiment. Before the euthanasia, the rats were weighed, sacrificed, and their kidneys were collected and weighed.

Then, the kidneys were embedded and the level of their fibrosis was confirmed by Masson's trichrome staining.

Additionally, in order to examine the expression levels of mRNAs and proteins of fibrosis-mediating materials α-SMA, TGF-β1, CTGF, ECM-related materials (type I collagen, fibronectin), Smad2/3, AKT, mTOR, and Snail, their mRNAs and proteins were isolated from renal tissues, quantitated, and subjected to RT-PCR and western blot analysis.

Additionally, the expression levels of fibrosis-mediating materials such as α-SMA, TGF-β1, and ECM-related materials (type I collagen, fibronectin) were observed by immunohistochemistry.

As a result, as is the case with the result in Experimental Example 3, it was confirmed that the expression levels of mRNAs and proteins of smad3, which is a fibrosis marker, and Snail were shown to increase due to the renal fibrosis induced by ureteral obstruction, however, in the case of the Group (UUO+drug), the expression levels of mRNAs and proteins of smad3 and Snail were shown to be reduced by the treatment with the biguanide derivative of Formula 1 according to the present invention.

A. In Vitro Experiment

For the in vitro experiment, proximal tubular cells and distal tubular cells were subjected to primary culture and used.

Experimental groups were divided into the following four groups:

1) Group treated with only a vehicle (sham); 2) Group treated with the biguanide derivative of Formula 1 (the compound of Example 44) according to the present invention to the vehicle (sham+drug); 3) Group treated with TGF-β1 (TGF-β1); and 4) Group treated with TGF-β1 followed by treatment with the biguanide derivative of Formula 1 (the compound of Example 44) according to the present invention (TGF-β1+HL156).

In order to examine the expression levels of mRNAs and proteins of CTGF, ECM-related materials (type I collagen, fibronectin), α-SMA, Smad2/3, AKT, mTOR, and Snail, their mRNAs and proteins were isolated, quantitated, and then subjected to RT-PCR and western blot analysis.

Additionally, the expression levels of fibrosis-mediating materials such as α-SMA and ECM-related materials (type I collagen, fibronectin) were observed by immunohistochemistry.

As a result of the experiment, as is the case with the animal experiment, it was confirmed that the expression levels of α-SMA, which is a marker for fibrosis, type I collagen, and fibronectin were increased. However, in the Group treated with the drug, the expression levels were shown to reduce by the treatment with the biguanide derivative of Formula 1 according to the present invention.

What is claimed is:

1. A method of preventing or treating fibrosis comprising administering a therapeutically effective amount of a N1-cyclic amine-N5-substituted biguanide derivative compound of Formula 1 below or a pharmaceutically acceptable salt thereof to a subject in need thereof:

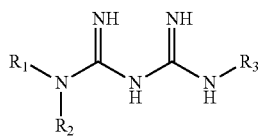

Formula 1 wherein $R_1$ and $R_2$ are taken together with nitrogen to which they are attached to form azetidinyl, pyrrolidinyl, piperidinyl, azepanyl, or dihydropyridinyl;
$R_3$ is $C_6$ aryl;
wherein $C_6$ aryl is unsubstituted or substituted with at least one non-hydrogen substituent selected from the group consisting of halogen, $C_{1-4}$ alkyl, and $C_{1-4}$ alkoxy, and the non-hydrogen substituent is unsubstituted or further substituted with halogen.

2. The method of claim 1, wherein $R_3$ is phenyl.

3. The method of claim 1,
wherein $R_1$ and $R_2$ are taken together with nitrogen to which they are attached to form azetidinyl, pyrrolidinyl, piperidinyl, or azepanyl; and
$R_3$ is phenyl unsubstituted or substituted with at least one non-hydrogen substituent selected from the group consisting of halogen, $C_{1-2}$ alkyl, and $C_{1-2}$ alkoxy, and the non-hydrogen substituent is unsubstituted or further substituted with halogen.

4. The method of claim 1,
wherein $R_1$ and $R_2$, are taken together with nitrogen to which they are attached to form azetidinyl, pyrrolidinyl, piperidinyl, or azepanyl; and
$R_3$ is phenyl,
wherein phenyl is unsubstituted or substituted with at least one non-hydrogen substituent selected from the group consisting of halogen, methyl, ethyl, methoxy, trifluoromethyl, difluoromethoxy, and trifluoromethoxy.

5. The method of claim 1,
wherein $R_1$ and $R_2$ are taken together with nitrogen to which they are attached to form dihydropyridinyl; and
$R_3$ is phenyl;
wherein phenyl is unsubstituted or substituted with at least one non-hydrogen substituent selected form the group consisting of halogen, hydroxy, $C_{1-4}$ alkyl, and $C_{1-4}$ alkoxy.

6. The method of claim 1,
wherein $R_1$ and $R_2$ are taken together with nitrogen to which they are attached to form azetidinyl, piperidinyl, or pyrrolidinyl; and
$R_3$ is phenyl;
wherein phenyl is unsubstituted or substituted with at least one non-hydrogen substituent selected from the group consisting of halogen, hydroxy, $C_{1-4}$ alkyl, and $C_{1-4}$ alkoxy.

7. The method of claim 1,
wherein $R_1$ and $R_2$ are taken together with nitrogen to which they are attached to form piperidinyl or pyrrolidinyl; and
$R_3$ is phenyl;
wherein phenyl is unsubstituted or substituted with a halogen.

8. A method of preventing or treating fibrosis comprising administering a therapeutically effective amount of a N1-cyclic amine-N5-substituted biguanide derivative compound or a pharmaceutically acceptable salt thereof to a subject in need thereof, wherein the compound is selected from the group consisting of:

N1-piperidine-N5-phenyl biguanide;
N1-piperidine-N5-(3-methyl)phenyl biguanide;
N1-piperidine-N5-(3-ethyl)phenyl biguanide;
N1-piperidine-N5-(3-methoxy)phenyl biguanide;
N1-piperidine-N5-(4-fluoro)phenyl biguanide;
N1-piperidine-N5-(3-fluoro)phenyl biguanide;
N1-pyrrolidine-N5-(4-chloro)phenyl biguanide;
N1-piperidine-N5-(4-chloro)phenyl biguanide;
N1-piperidine-N5-(3-bromo)phenyl biguanide;
N1-pyrrolidine-N5-(3-chloro)phenyl biguanide;
N1-piperidine-N5-(3-chloro)phenyl biguanide;
N1-azepane-N5-(3-chloro)phenyl biguanide;
N1-pyrrolidine-N5-(3-trifluoromethyl)phenyl biguanide;
N1-piperidine-N5-(3-trifluoromethyl)phenyl biguanide;
N1-pyrrolidine-N5-(4-trifluoromethyl)phenyl biguanide;
N1-piperidine-N5-(4-trifluoromethyl)phenyl biguanide;
N1-pyrrolidine-N5-(3-trifluoromethoxy)phenyl biguanide;
N1-piperidine-N5-(3-trifluoromethoxy)phenyl biguanide;

N1-piperidine-N5-(3-difluoromethoxy)phenyl biguanide;
N1-pyrrolidine-N5-(4-trifluoromethoxy)phenyl biguanide;
N1-piperidine-N5-(4-trifluoromethoxy)phenyl biguanide;
N1-piperidine-N5-(4-fluoro-3-trifluoromethyl)phenyl biguanide;
N1-piperidine-N5-(4-chloro-3-trifluoromethyl)phenyl biguanide;
N1-pyrrolidine-N5-(3-fluoro-4-trifluoromethyl)phenyl biguanide;
N1-piperidine-N5-(3-fluoro-4-trifluoromethyl)phenyl biguanide;
N1-piperidine-N5-(4-chloro-3-trifluoromethoxy)phenyl biguanide;
N1-azetidine-N5-(3-fluoro-4-trifluoromethoxy)phenyl biguanide;
N1-pyrrolidine-N5-(3-fluoro-4-trifluoromethoxy)phenyl biguanide;
N1-piperidine-N5-(3-fluoro-4-trifluoromethoxy)phenyl biguanide;
N1-azetidine-N5-(3-chloro-4-trifluoromethoxy)phenyl biguanide;
N1-pyrrolidine-N5-(3-chloro-4-trifluoromethoxy)phenyl biguanide;
N1-piperidine-N5-(3-chloro-4-trifluoromethoxy)phenyl biguanide;
N1-piperidine-N5-(3,4-difluoro)phenyl biguanide;
N1-piperidine-N5-(3,5-difluoro)phenyl biguanide;
N1-piperidine-N5-(3,5-dichloro)phenyl biguanide;
N1-pyrrolidine-N5-(3,4-dichloro)phenyl biguanide;
N1-piperidine-N5-(3,4-dichloro)phenyl biguanide;
N1-piperidine-N5-(3-chloro-5-trifluoromethoxy)phenyl biguanide;
N1-pyrrolidine-N5-(3-bromo-5-trifluoromethoxy)phenyl biguanide;
N1-piperidine-N5-(3-bromo-5-trifluoromethoxy)phenyl biguanide;
N1-piperidine-N5-(3,4,5-trifluoro)phenyl biguanide;
N1-pyrrolidine-N5-(4-trifluoromethyl)phenyl biguanide;
N1-piperidine-N5-(4-trifluoromethyl)phenyl biguanide;
N1-pyrrolidine-N5-(4-trifluoromethoxy)phenyl biguanide;
N1-piperidine-N5-(4-trifluoromethoxy)phenyl biguanide;
N1-pyrrolidine-N5-(3-fluoro-4-trifluoromethyl)phenyl biguanide;
N1-piperidine-N5-(3-fluoro-4-trifluoromethyl)phenyl biguanide;
N1-pyrrolidine-N5-(3-fluoro-4-trifluoromethoxy)phenyl biguanide;
N1-piperidine-N5-(3-fluoro-4-trifluoromethoxy)phenyl biguanide;
N1-piperidine-N5-(3-trifluoromethyl)benzyl biguanide;
N1-piperidine-N5-methyl biguanide;
N1-piperidine-N5-cyclohexyl biguanide;
N1-pyrrolidine-N5-cycloheptyl biguanide;
N1-piperidine-N5-cycloheptyl biguanide;
N1-azepane-N5-cycloheptyl biguanide;
N1-piperidine-N5-(4-methyl)benzyl biguanide;
N1-piperidine-N5-(4-methoxy)benzyl biguanide;
N1-pyrrolidine-N5-(4-chloro)benzyl biguanide;
N1-azepane-N5-(4-chloro)benzyl biguanide;
N1-piperidine-N5-(4-trifluoromethyl)benzyl biguanide;
N1-azetidine-N5-(4-trifluoromethoxy)benzyl biguanide;
N1-pyrrolidine-N5-(4-trifluoromethoxy)benzyl biguanide;
N1-piperidine-N5-(4-trifluoromethoxy)benzyl biguanide;
N1-piperidine-N5-(4-fluoro-3-trifluoromethyl)benzyl biguanide;
N1-piperidine-N5-(4-chloro-3-trifluoromethyl)benzyl biguanide;
N1-piperidine-N5-(3-fluoro-4-trifluoromethyl)benzyl biguanide;
N1-piperidine-N5-(3-chloro-4-trifluoromethyl)benzyl biguanide;
N1-piperidine-N5-(4-fluoro-3-trifluoromethoxy)benzyl biguanide;
N1-piperidine-N5-(3-chloro-4-trifluoromethoxy)benzyl biguanide;
N1-piperidine-N5-(2,6-difluoro)benzyl biguanide;
N1-piperidine-N5-(3,4-difluoro)benzyl biguanide;
N1-piperidine-N5-(2,4-dichloro)benzyl biguanide;
N1-pyrrolidine-N5-(3,4-dichloro)benzyl biguanide;
N1-piperidine-N5-(3,4-dichloro)benzyl biguanide;
N1-piperidine-N5-(thiophen-2-yl)ethyl biguanide;
N1-pyrrolidine-N5-(phenethyl) biguanide;
N1-piperidine-N5-(phenethyl) biguanide;
N1-azepane-N5-(phenethyl) biguanide;
N1-azepane-N5-((4-fluoro)phenethyl) biguanide,
N1-azepane-N5-((4-chloro)phenethyl) biguanide;
N1-1,2-dihydropyrrole-N5-(4-trifluoromethoxy)phenyl biguanide;
N1-1,2-dihydropyrrole-N5-(4-trifluoromethyl)phenyl biguanide;
N1-1,2-dihydropyrrole-N5-(3-trifluoromethyl)phenyl biguanide;
N1-1,2-dihydropyrrole-N5-(4-fluoro)phenyl biguanide;
N1-1,2-dihydropyrrole-N5-(4-chloro)phenyl biguanide;
N1-1,2-dihydropyrrole-N5-(4-bromo)phenyl biguanide;
N1-1,2-dihydropyrrole-N5-(3-chloro,4-trifluoromethoxy)phenyl biguanide;
N1-1,2,3,6-tetrahydropyridine-N5-(3-chloro,4-trifluoromethoxy)phenyl biguanide;
N1-1,2-dihydropyrrole-N5-(3-trifluoromethyl)benzyl biguanide;
N1-1,2-dihydropyrrole-N5-(4-trifluoromethyl)benzyl biguanide;
N1-1,2-dihydropyrrole-N5-(3-trifluoromethoxy)benzyl biguanide;
N1-(3-methyl)-1,2-dihydropyrrole-N5-(4-trifluoromethoxy)phenyl biguanide;
N1-(3-methyl)-1,2-dihydropyrrole-N5-(4-trifluoromethyl)phenyl biguanide;
N1-(3-methyl)-1,2-dihydropyrrole-N5-(4-chloro)phenyl biguanide;
N1-(3-methyl)-1,2-dihydropyrrole-N5-(4-chloro,3-trifluoromethyl)phenyl biguanide;
N1-(3-methyl)-1,2-dihydropyrrole-N5-(3-trifluoromethyl)phenyl biguanide;
N1-(3-methyl)-1,2-dihydropyrrole-N5-(4-fluoro)phenyl biguanide;
N1-(3-methyl)-1,2-dihydropyrrole-N5-(4-bromo)phenyl biguanide;
N1-(3-methyl)-1,2-dihydropyrrole-N5-(4-methoxy)phenyl biguanide;
N1-(3-methyl)-1,2-dihydropyrrole-N5-(3,4-dimethoxy)phenyl biguanide;
N1-(3-methyl)-1,2-dihydropyrrole-N5-(4-trifluoromethoxy)benzyl biguanide;
N1-(3-methyl)-1,2-dihydropyrrole-N5-(3-trifluoromethoxy)phenyl biguanide;
N1-(3-methyl)-1,2-dihydropyrrole-N5-(4-trifluoromethyl)benzyl biguanide;

N1-(3-methyl)-1,2-dihydropyrrole-N5-(4-chloro,3-trifluoromethyl)benzyl biguanide;
N1-1,2,3,6-tetrahydropyridine-N5-(4-trifluoromethoxy)phenyl biguanide;
N1-1,2,3,6-tetrahydropyridine-N5-(4-trifluoromethyl)phenyl biguanide;
N1-1,2,3,6-tetrahydropyridine-N5-(3-trifluoromethoxy)phenyl biguanide;
N1-1,2,3,6-tetrahydropyridine-N5-(3-trifluoromethyl)phenyl biguanide;
N1-1,2,3,6-tetrahydropyridine-N5-(4-fluoro,3-trifluoromethyl)phenyl biguanide;
N1-1,2,3,6-tetrahydropyridine-N5-(4-chloro,3-trifluoromethoxy)phenyl biguanide;
N1-1,2,3,6-tetrahydropyridine-N5-(3-fluoro,4-trifluoromethoxy)phenyl biguanide;
N1-1,2,3,6-tetrahydropyridine-N5-(4-chloro)phenyl biguanide;
N1-1,2,3,6-tetrahydropyridine-N5-(4-bromo)phenyl biguanide;
N1-1,2,3,6-tetrahydropyridine-N5-(4-fluoro)phenyl biguanide;
N1-1,2,3,6-tetrahydropyridine-N5-(3,5-dimethoxy)phenyl biguanide;
N1-1,2,3,6-tetrahydropyridine-N5-phenyl biguanide;
N1-1,2,3,6-tetrahydropyridine-N5-(4-methoxy)phenyl biguanide;
N1-1,2,3,6-tetrahydropyridine-N5-(3-methoxy)phenyl biguanide;
N1-1,2-dihydropyrrole-N5-(4-methoxy)phenyl biguanide;
N1-1,2-dihydropyrrole-N5-(3-methoxy)phenyl biguanide;
N1-1,2-dihydropyrrole-N5-phenyl biguanide;
N1-1,2-dihydropyrrole-N5-(3,5-dimethoxy)phenyl biguanide;
N1-1,2-dihydropyrrole-N5-(4-fluoro,3-trifluoromethyl)phenyl biguanide;
N1-1,2-dihydropyrrole-N5-(3-fluoro,4-trifluoromethyl)phenyl biguanide;
N1-1,2,3,6-tetrahydropyridine-N5-(4-methyl)phenyl biguanide;
N1-1,2,3,6-tetrahydropyridine-N5-(3-methyl)phenyl biguanide;
N1-1,2-dihydropyrrole-N5-(4-methyl)phenyl biguanide;
N1-1,2-dihydropyrrole-N5-(3-methyl)phenyl biguanide;
N1-1,2-dihydropyrrole-N5-(3-trifluoromethoxy)phenyl biguanide;
N1-1,2,3,6-tetrahydropyridine-N5-hexyl biguanide;
N1-1,2,3,6-tetrahydropyridine-N5-(4-trifluoromethoxy)benzyl biguanide;
N1-1,2,3,6-tetrahydropyridine-N5-(3-trifluoromethoxy)benzyl biguanide;
N1-1,2,3,6-tetrahydropyridine-N5-(4-trifluoromethyl)benzyl biguanide;
N1-1,2,3,6-tetrahydropyridine-N5-(3-trifluoromethyl)benzyl biguanide;
N1-1,2,3,6-tetrahydropyridine-N5-(4-chloro,3-trifluoromethyl)benzyl biguanide;
N1-1,2,3,6-tetrahydropyridine-N5-butyl biguanide;
N1-1,2,3,6-tetrahydropyridine-N5-propyl biguanide;
N1-1,2,3,6-tetrahydropyridine biguanide;
N1-(3-methyl)piperidine-N5-(3-trifluoromethyl)benzyl biguanide;
N1-(3-methyl)piperidine-N5-(4-chloro)benzyl biguanide;
N1-(3-methyl)piperidine-N5-(4-fluoro)phenyl biguanide;
N1-(3-methyl)piperidine-N5-(4-bromo)phenyl biguanide;
N1-(3-methyl)piperidine-N5-(4-chloro,3-trifluoromethyl)phenyl biguanide;
N1-(3-methyl)piperidine-N5-(3-fluoro,4-trifluoromethyl)phenyl biguanide;
N1-(3-methyl)piperidine-N5-(4-fluoro,3-trifluoromethyl)phenyl biguanide;
N1-(2-methyl)piperidine-N5-(4-trifluoromethoxy)phenyl biguanide;
N1-(2-methyl)piperidine-N5-(3-trifluoromethoxy)phenyl biguanide;
N1-(2-methyl)piperidine-N5-(4-trifluoromethyl)phenyl biguanide;
N1-(3-methyl)piperidine-N5-(3-fluoro,4-trifluoromethoxy)phenyl biguanide;
N1-(2-methyl)piperidine-N5-(3-fluoro,4-trifluoromethoxy)phenyl biguanide;
N1-(2-methyl)piperidine-N5-(4-chloro)phenyl biguanide;
N1-(2-methyl)piperidine-N5-(4-fluoro,3-trifluoromethyl)phenyl biguanide;
N1-(2-methyl)piperidine-N5-(3-trifluoromethyl)phenyl biguanide;
N1-(2-methyl)piperidine-N5-(4-chloro,3-trifluoromethyl)phenyl biguanide;
N1-(3-methyl)piperidine-N5-(4-trifluoromethyl)phenyl;
N1-(3-methyl)piperidine-N5-(4-trifluoromethoxy)phenyl biguanide;
N1-(3-methyl)piperidine-N5-(3-trifluoromethoxy)phenyl biguanide;
N1-(3-methyl)piperidine-N5-(4-trifluoromethoxy)benzyl biguanide;
N1-(3-methyl)piperidine-N5-(4-fluoro,3-trifluoromethyl)phenyl biguanide;
N1-(3-methyl)piperidine-N5-(4-trifluoromethyl)benzyl biguanide;
N1-(3-methyl)piperidine-N5-(4-chloro)phenyl biguanide;
N1-(3-methyl)piperidine-N5-(3-trifluoromethyl)phenyl biguanide;
N1-(2,6-dimethyl)piperidine-N5-(4-trifluoromethoxy)phenyl biguanide;
N1-(2,6-dimethyl)piperidine-N5-(3-trifluoromethoxy)phenyl biguanide;
N1-(2,6-dimethyl)piperidine-N5-(4-trifluoromethyl)phenyl biguanide;
N1-(2,6-dimethyl)piperidine-N5-(3-trifluoromethyl)phenyl biguanide;
N1-(2,6-dimethyl)piperidine-N5-(4-fluoro,3-trifluoromethyl)phenyl biguanide;
N1-(2,6-dimethyl)piperidine-N5-(4-chloro,3-trifluoromethyl)phenyl biguanide;
N1-(2,6-dimethyl)piperidine-N5-(3-fluoro,4-trifluoromethoxy)phenyl biguanide;
N1-(2,6-dimethyl)piperidine-N5-(4-chloro)phenyl biguanide;
N1-(2,6-dimethyl)piperidine-N5-(4-bromo)phenyl biguanide; and
N1-(2,6-dimethyl)piperidine-N5-(4-fluoro)phenyl biguanide.

9. The method of claim 1, wherein the pharmaceutically acceptable salt is a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methanesulfonic acid, dichloroacetic acid, aminooxyacetic acid, hydrochloric acid, bromic acid, sulfuric acid, phosphoric acid, nitric acid, carbonic acid, and boric acid.

10. The method of claim 1, wherein the fibrosis is at least one selected from the group consisting of liver fibrosis, renal fibrosis, pulmonary fibrosis, interstitial fibrosis, systemic scleroderma, macular degeneration, pancreatic fibrosis, spleen fibrosis, cardiac fibrosis, mediastinal fibrosis, myelofibrosis, vascular fibrosis, skin fibrosis, ocular fibrosis, arthrofibrosis, myofibrosis, thyroid fibrosis, endomyocardial fibrosis, peritoneal fibrosis, retroperitoneal fibrosis, progressive massive fibrosis, nephrogenic systemic fibrosis, post-operative fibrotic complication, and infection-associated fibrosis.

* * * * *